United States Patent
Aykol

(10) Patent No.: US 11,557,378 B2
(45) Date of Patent: Jan. 17, 2023

(54) SYNTHESIS ROUTE RECOMMENDATION ENGINE FOR INORGANIC MATERIALS

(71) Applicant: Toyota Research Institute, Inc., Los Altos, CA (US)

(72) Inventor: Muratahan Aykol, San Jose, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 440 days.

(21) Appl. No.: 16/867,973

(22) Filed: May 6, 2020

(65) Prior Publication Data

US 2021/0350880 A1     Nov. 11, 2021

(51) Int. Cl.
| | | |
|---|---|---|
| G16C 20/10 | (2019.01) | |
| G16C 20/80 | (2019.01) | |
| G16C 20/90 | (2019.01) | |
| G16C 60/00 | (2019.01) | |

(52) U.S. Cl.
CPC ............ *G16C 20/10* (2019.02); *G16C 20/80* (2019.02); *G16C 20/90* (2019.02); *G16C 60/00* (2019.02)

(58) Field of Classification Search
CPC ........ G16C 20/10; G16C 20/80; G16C 20/90; G16C 60/00
See application file for complete search history.

(56) References Cited

U.S. PATENT DOCUMENTS

| | | | |
|---|---|---|---|
| 9,757,706 | B2 | 9/2017 | Cronin |
| 9,962,677 | B2 | 5/2018 | Cronin |
| 2009/0024575 | A1* | 1/2009 | Wagner ................ G16C 20/10 |
| 2011/0106794 | A1* | 5/2011 | Hori ..................... G16C 20/10 707/723 |
| 2018/0101663 | A1* | 4/2018 | Botea ................... G16C 20/10 |

OTHER PUBLICATIONS

Alberi, K. et al., "The 2019 materials by design roadmap," J. Phys. D: Appl. Phys. 52 (2019) 49 pages.
Kim, E. et al., "Virtual screening of inorganic materials synthesis parameters with deep learning," npj Computational Materials (2017) 3:53, 9 pages.
Kononova, O. et al., "Text-minded dataset of inorganic materials synthesis recipes," Scientific Data (2019) 6:203, 11 pages.

\* cited by examiner

*Primary Examiner* — Lam S Nguyen
(74) *Attorney, Agent, or Firm* — Christopher G. Darrow; Darrow Mustafa PC

(57) ABSTRACT

A computer system and computational method for determining optimal solid-state methods for synthesis of an inorganic material that results in an output of recommended synthetic methods that can be implemented based on the recommendation. The method involves inputting a target inorganic material, querying structural data and thermodynamic data for the target inorganic material and reactant inorganic materials that can be used for its synthesis, enumerating possible synthetic reactions to construct a synthesis reaction database with a viable subset of the possible synthetic methods. The program generates a nucleation barrier metric and a competition metric that are combined to provide a recommendation of the synthetic procedures to the target inorganic material.

19 Claims, 29 Drawing Sheets

FIG. 8

Table. Sample reactions for synthesis of HT-LiCoO₂ (1000 K / 727 °C, air), selected from the recommender plot

| Reaction label | Reaction*** |
|---|---|
| R1* | 0.5 Li2O(mp-1960) + 0.0833 O2(mp-1091399) + 0.3333 Co3O4(mp-18748) |
| R2* | 0.0833 O2(mp-1091399) + 0.3333 Co3O4(mp-18748) + -0.5 CO2(mp-20066) + 0.5 Li2CO3(mp-3054) |
| R3* | 1.0 CoO(mp-22408) + -0.5 CO2(mp-20066) + 0.25 O2(mp-1091399) + 0.5 Li2CO3(mp-3054) |
| R4* | 0.5 Li2O(mp-1960) + -1.0 CO2(mp-20066) + 0.25 O2(mp-1091399) + 1.0 CoCO3(mp-21434) |
| R5* | -0.5 CO2(mp-20066) + 1.0 Co(mp-54) + 0.75 O2(mp-1091399) + 0.5 Li2CO3(mp-3054) |
| R6* | -1.5 CO2(mp-20066) + 0.25 O2(mp-1091399) + 0.5 Li2CO3(mp-3054) + 1.0 CoCO3(mp-21434) |
| R7 | 12.3333 O2(mp-1091399) + 1.0 LiCl2(mp-1021323) + 0.3333 Co3O4(mp-18748) + -12.0 CO2(mp-20066) |
| R8 | 0.3333 O2(mp-1091399) + 0.3333 Co3O4(mp-18748) + 1.0 Li(mp-135) |
| R9* | 1.0 CoO(mp-22408) + 0.5 Li2O2(mp-841) |
| R10** | 0.5 Li2O2(mp-841) + -1.0 CO2(mp-20066) + 1.0 CoCO3(mp-21434) |
| R11** | 0.3333 Li2O(mp-1960) + 0.1667 Li2O2(mp-841) + 0.3333 Co3O4(mp-18748) |
| R12** | 0.5 Li2O2(mp-841) + 0.25 Co3O4(mp-18748) + 0.25 Co(mp-54) |

*Established synthesis route (or a derivative of such a route) recovered by the recommender system.  Other promising novel routes suggested by the recommender system. *Minus (-) sign implies gas release alongside product. "mp-id" is the id of the compound in Materials Project database. For gasses, ids are irrelevant and exp. enthalpy and entropy values are used.

FIG. 16

Table. Sample reactions for synthesis of perovskite BaTiO$_3$ (1400 K / 1127 °C, air), selected from the recommender plot

| Reaction label | Reaction*** |
|---|---|
| R1* | 1.0 BaO(mp-1342) + 1.0 TiO2(mp-2657) |
| R2* | -1.0 CO2(mp-20066) + 1.0 TiO2(mp-2657) + 1.0 BaCO3(mp-4559) |
| R3 | 0.5 Ti2O3(mp-458) + 0.25 O2(mp-1091399) + -1.0 CO2(mp-20066) + 1.0 BaCO3(mp-5504) |
| R4 | 0.5 Ti2O3(mp-458) + 0.25 O2(mp-1091399) + 1.0 BaO(mp-1342) |
| R5 | 1.0 TiC(mp-631) + 2.0 O2(mp-1091399) + -2.0 CO2(mp-20066) + 1.0 BaCO3(mp-4559) |
| R6** | 1.0 BaO2(mp-1105) + 1.0 TiO(mp-1203) |
| R7 | 0.5 BaO2(mp-1105) + 0.5 Ti2O3(mp-458) + 0.5 BaO(mp-1342) |
| R8 | 1.0 BaO2(mp-1105) + 0.3333 Ti2O3(mp-458) + 0.3333 Ti(mp-72) |
| R9 | 1.0 BaO2(mp-1105) + 0.5 Ti2O3(mp-458) + -0.25 CO2(mp-20066) + 0.25 C(mp-568286) |
| R10* | 1.0 BaO2(mp-1105) + 0.5 Ti(mp-72) + 0.5 TiO2(mp-390) |

| Reaction label | Major competing products for R2 |
|---|---|
| R2b | -2.0 CO2(mp-20066) + 1.0 TiO2(mp-2657) + 2.0 BaCO3(mp-4559) yielding Ba2TiO4 (mp-3397) |
| R2c | -1.0 CO2(mp-20066) + 2.0 TiO2(mp-390) + 1.0 BaCO3(mp-4559) yielding BaTi2O5(mp-3943) |

| Reaction label | Retrosynthetic analysis |
|---|---|
| R11a | 0.5 BaO(mp-1342) + 0.5 BaTi2O5(mp-3943) |
| R11b | 1.0 BaO2(mp-1105) + 1.0 Ti2O3 (mp-458) |

*Established synthesis route (or a derivative of such a route) recovered by the recommender system. Other promising novel route suggested by the recommender system. *Minus (-) sign implies gas releases alongside product. "mp-id" is the id of the compound in Materials Project database. For gases, ids are irrelevant and exp. enthalpy and entropy values are used.

FIG. 21

Table. Sample reactions for synthesis of perovskite $YBa_2Cu_3O_7$ (1400 K / 1127 °C, air), selected from the recommender plot

| Reaction label | Reaction*** |
|---|---|
| R1* | 3.0 CuO(mp-1692) + 0.25 O2(mp-1091399) + 0.5 Y2O3(mp-2652) + 2.0 BaO(mp-1342) |
| R2* | 1.0 O2(mp-1091399) + 1.5 Cu2O(mp-361) + 0.5 Y2O3(mp-2652) + 2.0 BaO(mp-1342) |
| R3* | 3.0 Cu(mp-30) + 1.75 O2(mp-1091399) + 0.5 Y2O3(mp-2652) + 2.0 BaO(mp-1342) |
| R4* | -2.0 CO2(mp-20066) + 3.0 CuO(mp-1692) + 0.25 O2(mp-1091399) + 0.5 Y2O3(mp-2652) + 2.0 BaCO3(mp-4559) |
| R5* | 2.0 BaO2(mp-1105) + 1.5 Cu2O(mp-361) + 0.5 Y2O3(mp-2652) |
| R6** | 2.0 BaO2(mp-1105) + 1.0 Y(mp-112) + 3.0 CuO(mp-1692) |
| R7** | 0.5 BaO2(mp-1105) + 3.0 CuO(mp-1692) + 1.5 BaO(mp-1342) + 0.5 Y2O3(mp-2652) |
| R8*,** | 2.0 BaO2(mp-1105) + 3.0 CuO(mp-1692) + -0.75 O2(mp-1091399) + 0.5 Y2O3(mp-2652) |
| R9*,** | 0.25 O2(mp-1091399) + 0.5 Y2Cu2O5(mp-2882) + 2.0 BaCuO2(mp-997034) |
| R10** | 0.5 Cu2O(mp-361) + 0.5 Y2O3(mp-2652) + 2.0 BaCuO2(mp-997034) |
| R11*,** | 2.0 Cu(mp-30) + -2.0 CO2(mp-20066) + 1.25 O2(mp-1091399) + 2.0 BaCO3(mp-4559) + 0.5 Y2Cu2O5(mp-2882) |
| R12** | 2.0 CuO(mp-1692) + 2.0 BaO(mp-1342) + 0.25 O2(mp-1091399) + 0.5 Y2Cu2O5(mp-2882) |

*Established synthesis route (or a derivative of such a route) recovered by the recommender system. Other promising novel route suggested by the recommender system. *"Minus (-) sign implies gas release alongside product. "mp-id" is the id of the compound in Materials Project database. For gasses, ids are irrelevant and exp. enthalpy and entropy values are used.

SYNTHESIS ROUTE RECOMMENDATION ENGINE FOR INORGANIC MATERIALS

TECHNICAL FIELD

The present disclosure generally relates to a computational method for determination of multiple solid-state preparation routes for a target inorganic material that enables their comparison and prioritization on the basis of synthetic efficiency in producing the target material, and output highly probable synthesis processes that can be used to direct targeted synthesis of the inorganic material.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Synthesis design for crystalline inorganic materials of a targeted polymorphic form is extremely challenging, particularly for solid-state synthesis from available reactants (starting materials or precursors). Computational systems for design of organic small molecule synthesis (e.g. drug design) have been realized and implemented (e.g. retrosynthetic analysis) from databases available and/or generated sets of known solution reactions that can be incrementally applied to achieve a target molecule. No such broad and computationally accessible reaction selection and prioritization strategy and method currently exists for crystalline inorganic solid materials.

The number of combinatorial possibilities of crystal structures and compositions that define the space of inorganic materials is enormous, and the resulting number of polymorphic forms for any single material composition further adds to the challenge of designing structures that achieve desired properties and their synthesis from available inorganic materials. Given the massive number of possibilities for materials and synthetic routes that can lead to their formation, the design process is well suited to the ability of computer algorithms to consider from the possibilities in a time frame that is rather inconceivable for strictly human inspection and design. Hence, a system and method to identify viable and efficient synthetic routes that provide access to new inorganic materials or polymorphs or alternative routes for existing/known inorganic materials or polymorphs is desirable. The ability of such a system to input information for targets and starting materials/precursors to these targets from available material structure and thermochemistry databases and output the synthetic methods for use in solid-state laboratory experiments and/or with robotic systems for the synthesis of the products is desirable.

SUMMARY

This section provides a general summary of the disclosure and is not a comprehensive disclosure of its full scope or all its features.

In various aspects, the present teachings provides a synthesis route recommendation engine including an input device for receiving and selecting a target inorganic material and optional arguments on which thermodynamic conditions or starting material/precursor classes to consider, which are provided to one or more processors having a memory communicably coupled to the processors for storing computed data and data acquired from one or more structural and thermodynamics databases of a remote computer. The engine employs a synthesis reaction enumerator module including instructions that cause the processors to enumerate a plurality of possible synthetic reactions leading to the target inorganic material from data acquired from the material (structural and thermodynamics) databases and store a synthesis reaction database to the memory. The engine employs a nucleation estimator module including instructions that cause the one or more processors to compute similarity values and to identify epitaxially matching facets for starting materials/precursors and the target inorganic material, compute the energies of the enumerated synthesis reactions from these starting materials under thermodynamic conditions input by the user, if available, or otherwise under default conditions of the system and store a viable subset of synthetic reactions, and use these computed values to generate and store a nucleation barrier metric for each synthetic reaction of the viable subset. The engine employs a competition module that includes instructions that cause the one or more processors to compute a number of possible thermodynamically competing phases other than the target material that could result from each enumerated synthetic reaction's reactants, and generates and stores a competition metric for each synthetic reaction of the viable subset. Ultimately a recommendation visualizer module includes instructions that cause the one or more processors to generate a recommendation plot displaying the nucleation barrier metric and the competition metric for the viable synthetic reactions and store this information in a human or machine-readable file.

In other aspects, the present teachings provide a computational method to determine an optimal solid-state synthetic method for synthesis of a target inorganic material. After receiving a target inorganic material, and arguments on which thermodynamic conditions and starting material/precursor subclasses to consider from a user or from an output from a program in a processor, structural data and thermodynamic data for the target inorganic material and possible starting materials/precursors that can be used in its synthesis are queried from any material database, allowing possible synthetic reactions for the target inorganic material to be enumerated in a synthesis reaction enumerator module. Subsequently, a synthesis reaction database is constructed for the target inorganic material. Each of the synthetic reactions is entered into a competing phase finder module and a nucleation estimator module. The nucleation estimator module is configured to acquire thermodynamic data such as enthalpy and entropy for each material in each reaction and compute the reaction energies under user-specified thermodynamic conditions or the default thermodynamic conditions of the system and store information on which reactions form a viable subset, and to compute similarity values for reactants and the target inorganic material for each synthetic reaction of the viable subset. Epitaxially matching facets for the reactants and the target inorganic material are identified for each synthetic reaction within the synthesis reaction database that are determined to be viable. From these, a nucleation barrier related metric is computed for each synthetic reaction of the viable subset in the nucleation estimator module. The number of possible thermodynamically competing phases other than the target material that could result from each enumerated synthetic reaction's reactants is computed for each synthetic reaction that was determined to be in the viable subset, and stored as a competition metric in the competition module. From these computations a recommendation visualizer is presented to a user in a mode displaying recommended synthetic reactions where the output of the nucleation estimator module is given as the nucleation barrier metric and the output from the competing phase module is given as the competition metric, enabling a user or a downstream program to distinguish more favorable reactions for the synthesis of the target material from less favorable ones effectively.

In another aspects, the present teachings provide a non-transitory computer-readable medium for determining an optimal solid-state synthetic method for synthesis of a target inorganic material and storing instructions that, when executed by one or more processors, receives a target inorganic material and arguments on which thermodynamic conditions and starting material/precursor subclasses to consider from a user or from an output from a program in a processor and queries structural data and thermodynamic data for the target inorganic material from material databases. The possible synthetic reactions for the target inorganic material are enumerated in a synthesis reaction enumerator module upon inputting structural data and thermodynamic data to the synthesis reaction enumerator module for the starting materials/precursors from any material database. This allows construction of a synthesis reaction database for the target inorganic material. Each synthetic reaction of the synthesis reaction database is entered into a competing phase finder module and a nucleation estimator module. The nucleation estimator module is configured to acquire thermodynamic data such as enthalpy and entropy data for each material in each reaction, compute the reaction energies under user-specified thermodynamic conditions or the default thermodynamic conditions of the system and determine a viable subset of synthesis reactions, to compute similarity values for reactants and the target inorganic material for each synthetic reaction of the viable subset from structural data contained within the synthesis reaction database, and to identify epitaxially matching facets for the reactants and the target inorganic material for each synthetic reaction of the viable subset within the synthesis reaction database. From this a nucleation barrier related metric is computed for each synthetic reaction of the viable subset in the nucleation estimator module. Additionally, the number of possible thermodynamically competing phases for each viable synthetic reaction is generated as a competition metric in a competing phase finder module. Results of the nucleation estimator module, as the nucleation metric, and results from the competing phase finder module, as the competition metric, are output to a recommendation visualizer where the viable subset is presented to the user or a downstream program in a mode displaying recommended synthetic reactions, enabling a user or downstream program to distinguish effectively more favorable reactions from less favorable reactions for the synthesis of the target material.

Further areas of applicability and various methods of enhancing the above coupling technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein:

FIG. 8 shows the sample reactions labeled in FIGS. 4 to 7 for solid-state HT-$LiCoO_2$ synthesis.

FIG. 16 shows the sample reactions labeled in FIGS. 9 to 15 for solid-state synthesis of perovskite $BaTiO_3$ or related intermediates.

FIG. 21 shows the sample reactions labeled in FIGS. 17 to 19 for solid-state synthesis of $YBa_2Cu_3O_7$.

It should be noted that the figures set forth herein are intended to exemplify the general characteristics of the methods, algorithms, and devices among those of the present technology, for the purpose of the description of certain aspects. These figures may not precisely reflect the characteristics of any given aspect and are not necessarily intended to define or limit specific embodiments within the scope of this technology. Further, certain aspects may incorporate features from a combination of figures.

DETAILED DESCRIPTION

The present teachings provide for a synthesis route recommendation engine that has an empirical and computational data-driven architecture from which solid-state synthetic routes can be identified for an input target inorganic material selected for development, where, in the present context, a material is defined on the basis of its crystal structure and chemical composition. The input material can be one queried by a user or computer identified material based on the needs of the user. The input material allows inspection and input from material databases to establish enumerated reaction stoichiometry that can form the target material.

The presently disclosed synthesis route recommendation engine performs a computational method for inorganic synthesis identification that allows a user or programmed input that defines a desired end or beginning of a synthetic procedure, where a preferred reactant, either a starting material or a precursor of a particular synthesis reaction, or a desired target inorganic material is input. As disclosed herein, the program will be described for an identified target that is selected to achieve a functionality required for a product or method needed by the user rather than from the position of a reactant supplier whose goal is the generation of downstream products, where after identification of the target products, synthesis are identified in a manner equivalent to that where the input is of a target product.

Figure 1:
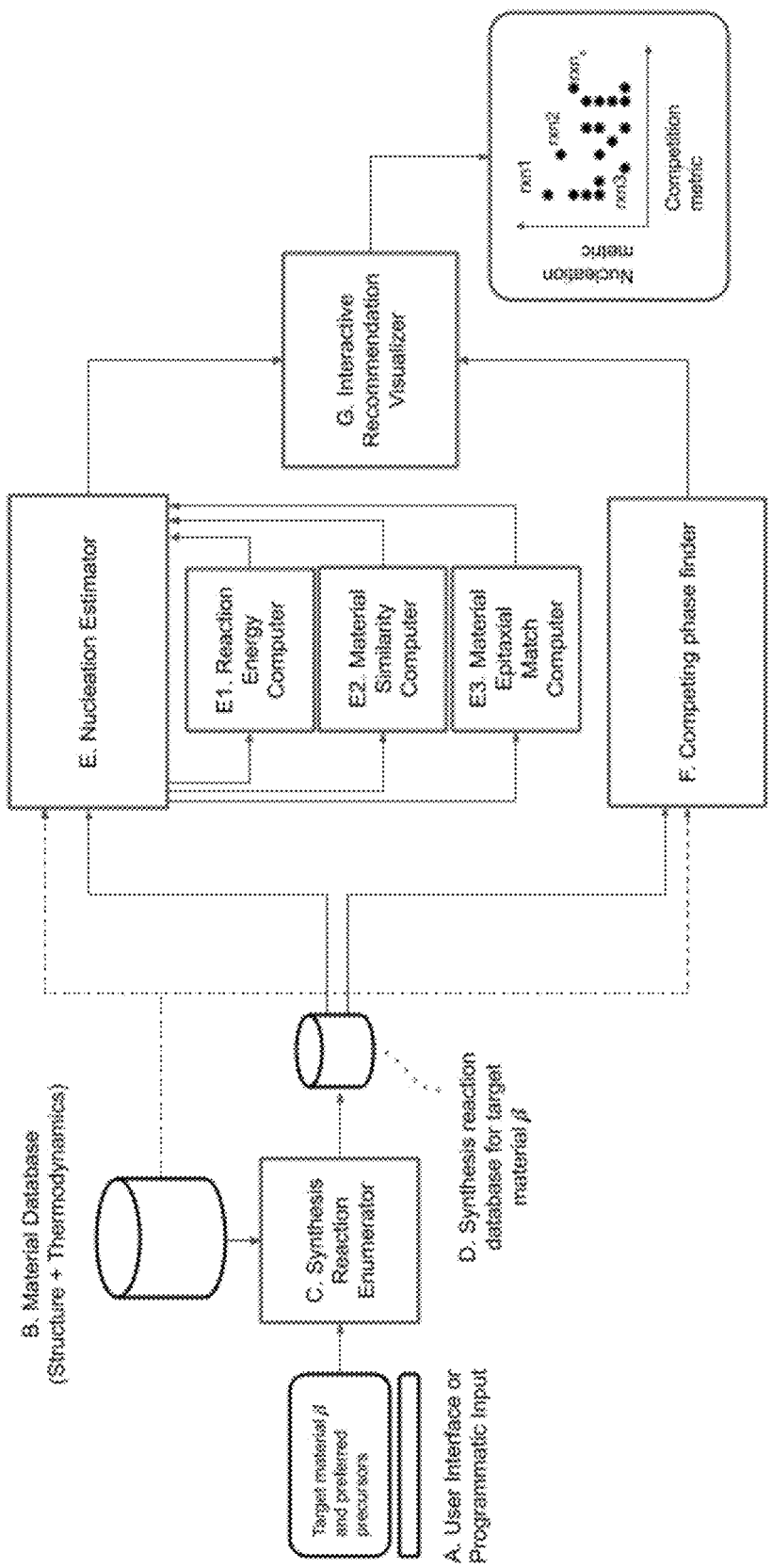
FIG. 1 shows a flow chart for an inorganic synthesis identifying program from the input of a target inorganic material $\beta$, through the output of route recommendations for the synthesis of $\beta$.

The programmed input can be from a user interface or generated in a routine that identifies inorganic materials that possess some desired property or structure. Upon this input to the program interface (A) an analysis of possible synthetic strategies ensues, as is illustrated in FIG. 1 where the various modules employed for generating and comparing data and the modules connectivity are illustrated. The primary input of the target is provided to a synthesis reaction enumerator (C), where all balanced reactions from all possible reactants to the target inorganic material are enumerated.

As indicated in FIG. 1, the enumerator (C) queries and receives input from a database of materials (B). The database is of structural and/or thermochemical data that can be of empirical thermodynamic data, which is tabulated or otherwise readily retrieved, or from first-principle computations, such as that available on the world wide web from Materials Project, Open Quantum Materials Database, AFLOW database, or is calculated within the domain of the processor or accessible computation systems that is used for the enumeration. All materials that are made of some or all the elements contained in the target material are retrieved as possible reactants from these databases or calculations. If specified as a condition by the user, elements that may not necessarily be a component in the target but are generally abundant in common starting materials/precursors such as C, N, O, H, etc. can be included in reactant querying from databases hence allowing different subclasses of starting materials/precursors such as carbonates, nitrates, hydroxides etc. to be included as part of possible reactants, and reactions including such reactants can be balanced by allowing the release of the added element along with the target as a removable byproduct, for example in the form of a gas, such as $CO$, $CO_2$, $H_2O$, or $NO_2$. The enumerator can also store the thermodynamic properties of the products and reactants acquired from materials databases for the balanced synthesis equations in database (D) to later provide to downstream modules. The enumeration can include those for transformations from readily available starting materials to the reactants or intermediates used as input for the reaction enumerated, hence, a plurality of transformations from starting materials through intermediates to the target inorganic material can be conducted. The output of the reaction enumerator can be stored in a synthesis database (D) in a computationally accessible form.

Each of the enumerated reactions from the synthesis reaction database (D) can be delivered to two computational subsystems that perform as a nucleation estimator (E) and as a competing phase finder (F). These two subsystems are programmed to query and retrieve thermochemical data as needed from the database of materials (B) or access that date via the reaction database (D). The two subprograms provide complementary information concerning the outcome and viability of the chemical transformation being calculated for the input provided by the synthesis database (D).

The nucleation estimator (E) carries out three series of calculations to estimate a metric proportional to the barrier of nucleation to a phase of target inorganic material β. E1 acquires thermodynamic data, including enthalpy and entropy data from the reaction database (D) and/or from material property database (B) for entries in reactions and, calculates the reaction energies, and can apply empirical corrections to calculated data to ensure the data's reliability. In calculating the reaction energy, often the enthalpy data is the major contribution from the solid phases and their entropy contribution can be neglected as a reasonable approximation, whereas entropy contribution is often non-negligible for gases at finite temperatures of interest and, hence, should be included and are available from standard thermodynamic tables/databases. E1 can apply such contributions of the user-specified thermodynamic conditions, for example, temperature and gas pressure, using common thermodynamic formalisms to ensure those conditions are reflected in the calculated free energy of the synthetic reaction. E2 computes a similarity value for every reactant and the target inorganic material β from crystal structure information using either descriptors of the material composition and its crystal structure or crystal structure representation methods for each reaction stored in synthetic database (D). The similarity value can be obtained from an inverse dependence on a distance, such as a Euclidean distance, Manhattan distance, or Cosine distance, measured in a high-dimensional space provided by the input crystal structure data, where shorter distances result for similar materials and longer distances for dissimilar materials, and in turn similar materials have higher similarity values and dissimilar materials have lower similarity values. Alternatively, the similarity values could be obtained directly from similarity metrics, such as Tanimoto similarity and Dice similarity. An output similarity value is stored for each reactant and the target material β for all enumerated reactions in the synthetic database D. E3 finds epitaxially matching facets for the reactants and target inorganic material β from the calculated structures for every reaction in the synthetic database D that was generated. Methods similar to that disclosed in: Zur et al., *Journal of Applied Physics* 55 (1984) 37, are useful for identifying epitaxially matching facets. An epitaxial matching quantity can be generated as a minimal matching area or a derived score. Materials that have matching epitaxial relationships or minimal matching area for epitaxial matching, have a higher score than those that do not. Output from E1, E2, and E3 are used to compute a nucleation barrier related metric for each reaction that forms the target inorganic material $\beta$.

Computation of the nucleation barrier related metric begins from classical nucleation theory (CNT), where the rate of nucleation of a new phase $\beta$ is proportional to two exponential terms expressed as:

$$\hat{N} \sim \exp(-\Delta G^*/kT) \cdot \exp(-\Delta E_d/kT), \quad \text{Eq. 1}$$

where $\Delta G^*$ is the critical energy barrier for nucleation and whose minimization favors nucleation. $\Delta E_d$ is a barrier term for transport of species that has a similar effect. The nucleation estimator (E) system searches reactions with small $\Delta G^*$ to the target inorganic material $\beta$ to yield large nucleation rates. $\Delta G^*$ is minimized where nucleation is heterogeneous, that being on the surface of another material. Nucleation rates are at a maximum using reactants that have an optimal balance between bulk reaction energy $\Delta G_x$, as computed in E1, and surface/interphase energy penalties, which is where the synthetic reaction has the smallest $\Delta G^*$ value. Depending on the targeted synthesis approach, as will be addressed below, $\Delta E_d$ is optionally included as a penalty term if transport can be a bottleneck of the synthesis of the target material.

Figure 2:
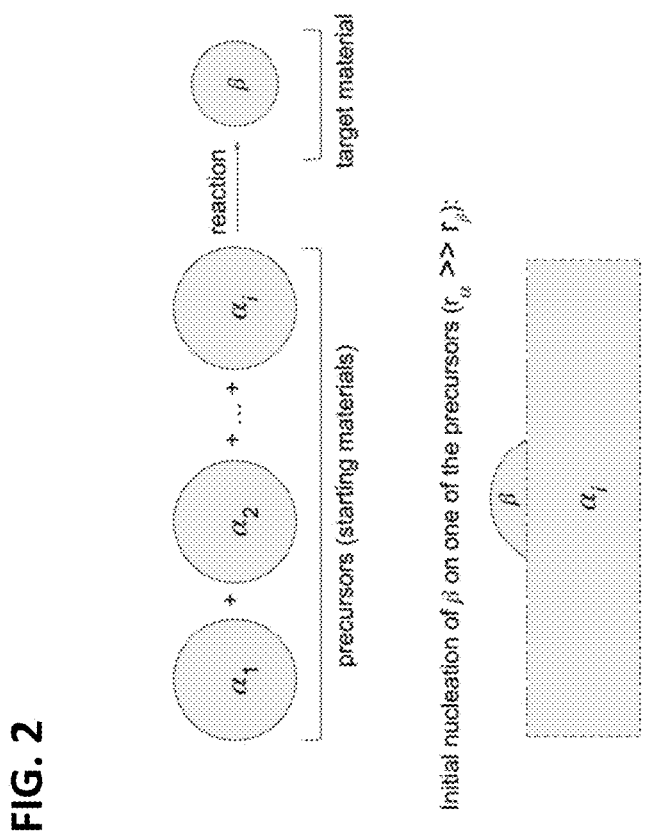
FIG. 2 shows how each of a plurality of synthetic methods is analyzed based on the initial nucleation of the target inorganic material $\beta$ for each of the reactants.

The inorganic synthesis identifying program constrains the output to the target inorganic material $\beta$ to those conditions where the synthesis happens in contact with at least one solid reactant such that heterogeneous nucleation of $\beta$ can take place on the reactant's surface. As illustrated in FIG. 2, each reactant $\alpha_i$ is identified and evaluated for nucleation of target $\beta$. For $\beta$ nucleating on one of the precursors $\alpha_i$, evaluation is carried out using:

$$\Delta G^*[\beta \text{ on } \alpha_i] = 16\pi/3 \cdot \gamma_{\beta\nu}{}^3/\Delta G_x{}^2 \cdot f[S(\beta \text{ on } \alpha_i)] \quad \text{Eq. 2}$$

where $\alpha G_x$ is the bulk thermodynamic reaction energy for the transformation where one of the reactants is $\alpha_i$, which can be approximated as energy of synthesis reaction x per volume of $\beta$, that is obtained from the experimental and/or computational databases with high accuracy and/or from a database of materials and their properties (B) for each reaction stored in the synthetic database (D). Thermodynamic conditions input by the user, for example, target temperatures and gas pressures, can be accounted for in computation of $\Delta G_x$, as address above. The term $\gamma_{\beta\nu}$ is the surface energy of target phase $\beta$ (between $\beta$ and vacuum or $\beta$ in the synthesis environment) and a property of the phase $\beta$ only. For the synthetic architecture described here as governed by Eq. 2, the relative ranking of different synthesis reactions for their $\Delta G^*$ for $\beta$ on $\alpha_i$ clearly does not depend on knowing an absolute value of $\gamma_{\beta\nu}$. Therefore, for a relative comparison of $\Delta G^*$ values pertaining to different synthetic reactions and their constituent reactants a only factors that must be quantified or approximated are $\Delta G_x$ and the scaling factor: $f[S(\beta \text{ on } \alpha_i)]$.

As shown in FIG. 2, the initial formation of phase $\beta$ occurs with nucleation on one of its reactants, $\alpha_i$. Any curvature of the precursor surface can be neglected, and the traditional equation of heterogeneous CNT for a spherical cap on a flat surface can be used, where the term $f$ can be described as:

$$f[S(\beta \text{ on } \alpha_i)] = (2 - 3S(\beta \text{ on } \alpha_i) + S(\beta \text{ on } \alpha_i)^3)/4 \quad \text{Eq. 3}$$

Here $-1 \leq S(\beta \text{ on } \alpha_1) \leq 1$ and, hence, $0 \leq f[S(\beta \text{ on } \alpha_1)] \leq 1$. A small value of $f[S(\beta \text{ on } \alpha_1)]$ results in a low value of $\Delta G^*$ [$\beta$ on $\alpha_i$], which favors nucleation. The value of $S(\beta \text{ on } \alpha_1)$ relates to the surface and interfacial energies by the equation:

$$S(\beta \text{ on } \alpha_i) = (\gamma_{\alpha\nu} - \gamma_{\beta\alpha})/\gamma_{\beta\nu} \quad \text{Eq. 4}$$

Absolute values of $\gamma$ for all possible synthesis reactions are intractable to measure or compute. However, similar $\alpha_i$ and $\beta$ structures, and such structures having matching epitaxial relationships can result in higher S values compared to other pairs, and can have S approaching 1 for highly similar and epitaxially matching structures (S→1), which results in a small $f$. This scenario allows the definition of the range of interest to be where $\gamma_{\alpha\nu}$ and $\gamma_{\nu\beta}$ are close, hence the similarity of structures, and $\gamma_{\beta\alpha}$ is as small as possible, hence similarity and epitaxial matching of structures. This allows an approximation of S defined in Eq. 4 as a deviation from its ideal value of 1 as:

$$S(\beta \text{ on } \alpha_i) \approx 1 - q(\beta, \alpha_i) \quad \text{Eq. 5}$$

where $q(\beta, \alpha_i)$ is a function that approximates the deviation related to the degree of similarity and epitaxially-relatedness of $\beta$ and $\alpha_i$, and q yields a positive value with the ideal value being 0 for exact similar/epitaxial matches of the $\beta$ and $\alpha_i$ structures.

Standardized and/or normalized (to interval [0,1]) quantities of structural similarity and minimal epitaxial matching area can be used for epitaxial matching, namely $q_{sim}$ and $q_{epi}$ that are combined with equal weights to obtain q in Eq. 5. Models can be used for calculation of actual values of $\gamma$. However, since reactant materials that can preferably nucleate the target relative to the others are the ones that system prefers and needs to identify, finding reactant materials that would maximize S, closer to 1 in the form $1 - q(\beta, \alpha_i)$, as above, is adequate for a data-driven reaction screening. Among the $S(\beta \text{ on } \alpha_1)$ values calculated for a given reaction corresponding to each reactant $\alpha_1$ the reaction has, the smallest S can be assigned to the reaction.

As indicated above, depending on the targeted synthesis approach, $\Delta E_d$ can be omitted or included if transport is considered as a bottleneck in synthesis of target $\beta$. If synthesis occurs in a way that facilitates transport the term can be omitted. Where transport is limited by the phases, being exclusively a solid-state reaction, inclusion is made using the approximation:

$$\Delta E_d \sim C \times q_{sim} \quad \text{Eq. 6}$$

where, similar structures have a lower $\Delta E_d$ value and C is a constant that is given a value such as 10 eV, which would yield a high transport barrier for dissimilar structures and a low transport barrier for similar structures. Here $q_{sim}$ pertaining to $\alpha_i$, whose S is assigned to the reaction, or a certain aggregation of $q_{sim}$ of all reactants, for example, a mean, can be used. These parameters can be further optimized.

The parameters $\Delta G^*$ and, optionally, $\Delta E_d$ are used to compute a metric $\Delta G_b$ which approximates a relative barrier to nucleation of the target material for each reaction:

$$\Delta G_b \sim \Delta G^* + \Delta E_d \quad \text{Eq. 7}$$

The $\Delta G_b$ value serves as a nucleation barrier metric, in the light of Eq. 1, where lower values indicate more favorable nucleation of $\beta$. If user-specified thermodynamic conditions exist, for example, temperature and pressure, their effects can be included when data is available, particularly as part of reaction energy $\Delta G_x$ in $\Delta G^*$. As explained above, to a first approximation, entropy effects are neglected for solid compounds or elements. Entropy and enthalpy contributions, as controlled by temperature and pressure, are included from available tabulated data and common thermodynamic formalisms for gaseous molecules, such as $O_2$, $N_2$, $H_2$, $F_2$, CO, and $CO_2$, included in the balanced reactions. As a primary requirement, $\Delta G_x$ has to be negative under the given thermodynamic conditions for the reaction to progress and hence be considered as viable and passed to later stages; otherwise, the reaction is labeled as "not viable", and excluded from further analysis.

Although maximizing nucleation rate is a focus for synthesis of a target inorganic material β phase, the same reactants can lead to nucleation of other phases than β and is not addressed by the computations to maximize the nucleation rate. Cross-phase comparison of nucleation rates for all possible products from a given set of reactants requires quantitative values for surface and interface energies and is impractical. For this reason, the competing phase finder F is employed.

Figure 3:
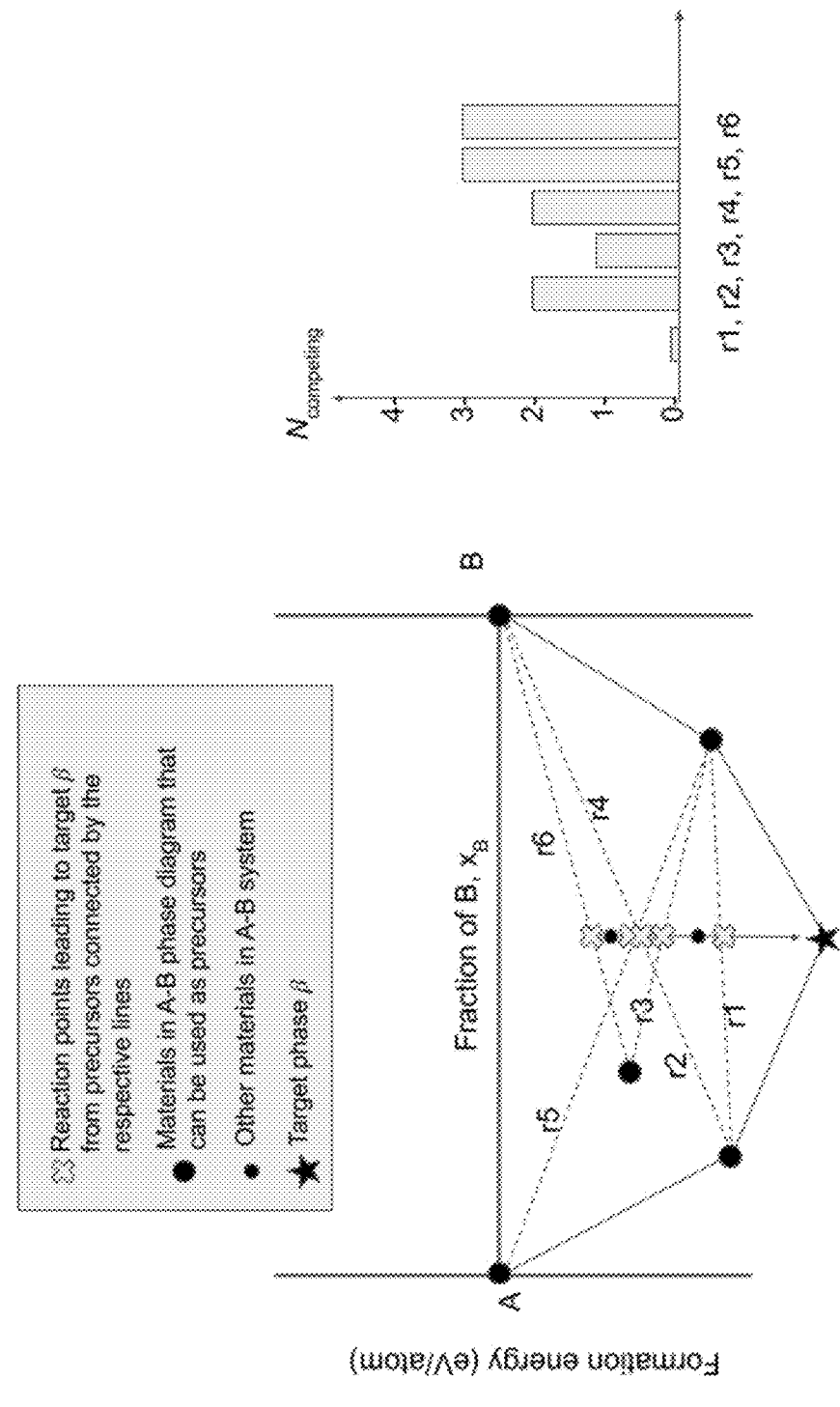
FIG. 3 is illustrative of an energy-composition diagram for identification of possible competing phases during a synthesis of a target inorganic material $\beta$ and a bar graph of the counts of viable competing phases thermodynamically accessible from a mixture of the reactants of each reaction targeting $\beta$.
Figure 4:
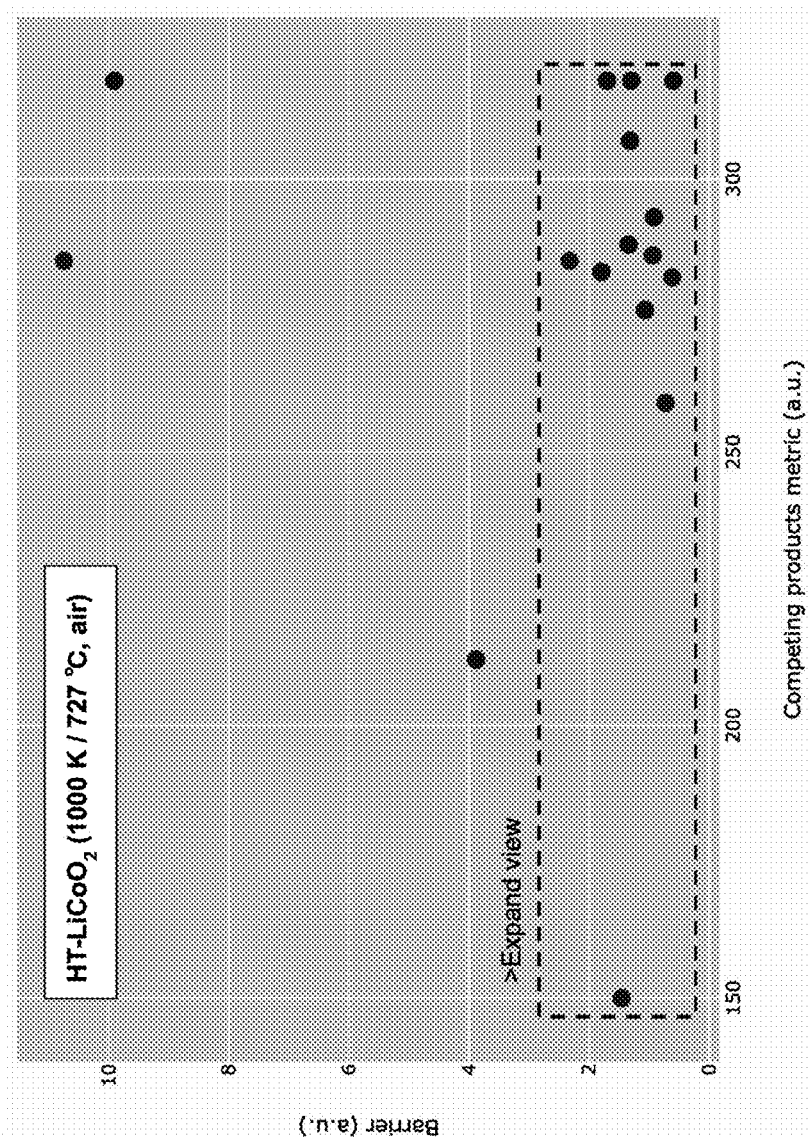
FIG. 4 is an exemplary output for the inorganic synthesis route identifying program for the synthesis of high-temperature (HT) form of layered $LiCoO_2$ under typical, exemplary thermodynamic conditions from common oxide, carbonate and other carbon-bearing starting materials, where the recommended procedures are those relatively closer to the origin of the plot and points forming or near the pareto frontier, and a display for the option to select and expand the region of interest of the plot is shown, where the expansion is separately viewed in FIG. 5.
Figure 5:
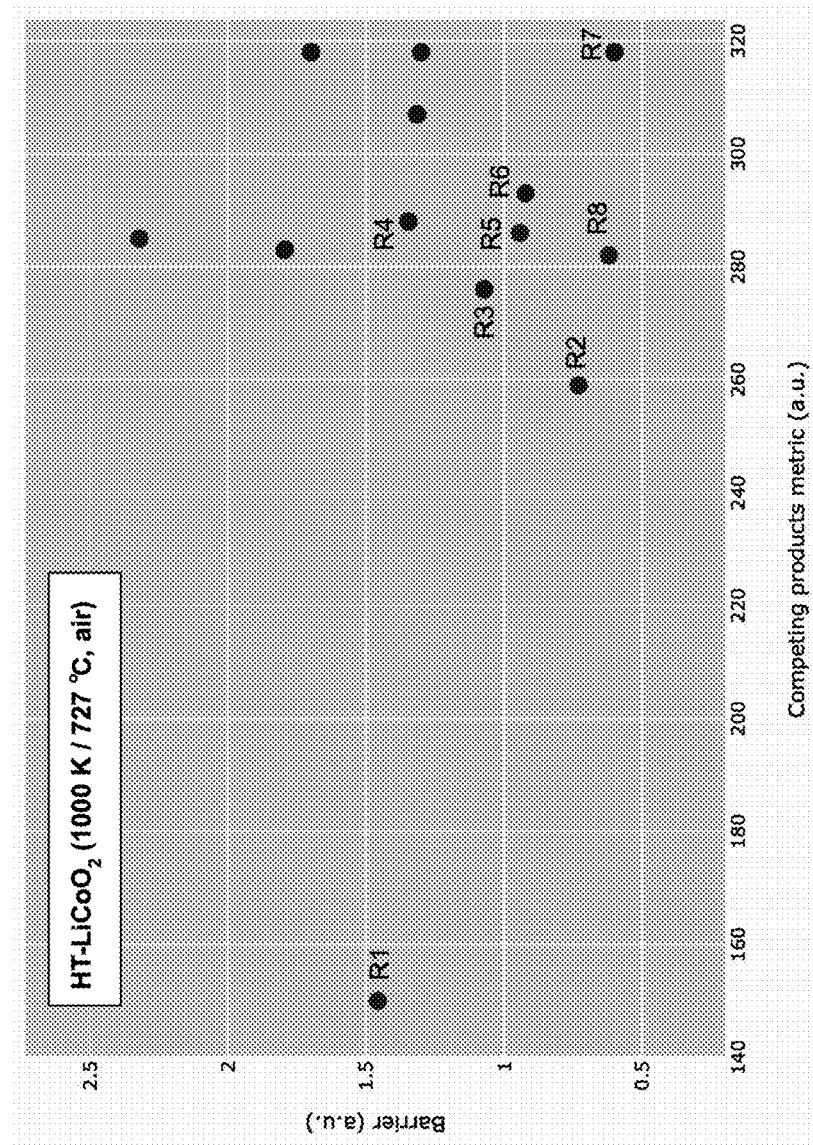
FIG. 5 is the selected region display of the recommendation plot of HT-$LiCoO_2$ displayed in FIG. 4, where several exemplary reactions are labeled, a list of which is provided in FIG. 8; and where the recommended procedures are those relatively closer to the origin of the plot and points forming or near the pareto frontier.
Figure 6:
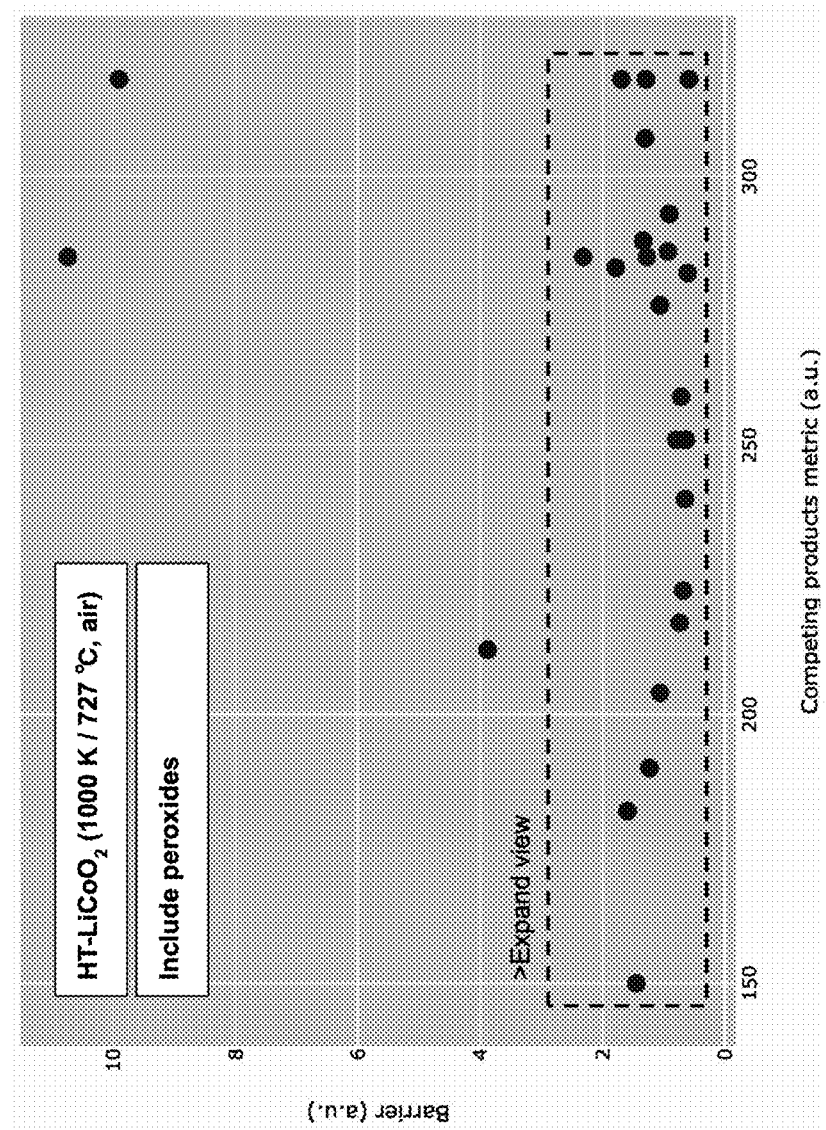
FIG. 6 is an exemplary output for the inorganic synthesis route identifying program for HT-$LiCoO_2$ synthesis under typical, exemplary thermodynamic conditions from common oxide, carbonate and other carbon-bearing starting materials as well as metal peroxides, where the recommended procedures are those relatively closer to the origin of the plot and points forming or near the pareto frontier, and a display for the option to select and expand the region of interest of the plot is shown, where the expansion is separately viewed in FIG. 7.
Figure 7:
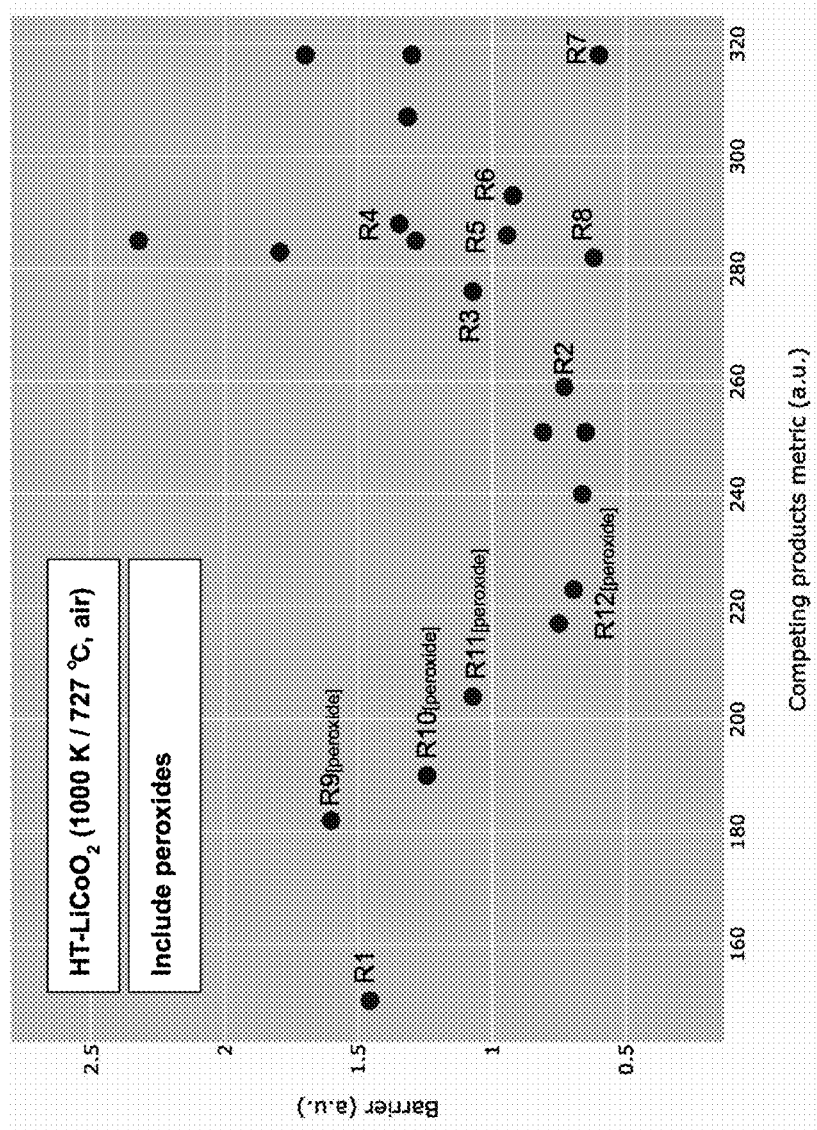
FIG. 7 is the selected region display of the recommendation plot of HT-$LiCoO_2$ displayed in FIG. 6, where several exemplary reactions are labeled, a list of which is provided in FIG. 8; and where the recommended procedures are those relatively closer to the origin of the plot and points forming or near the pareto frontier.
Figure 9:
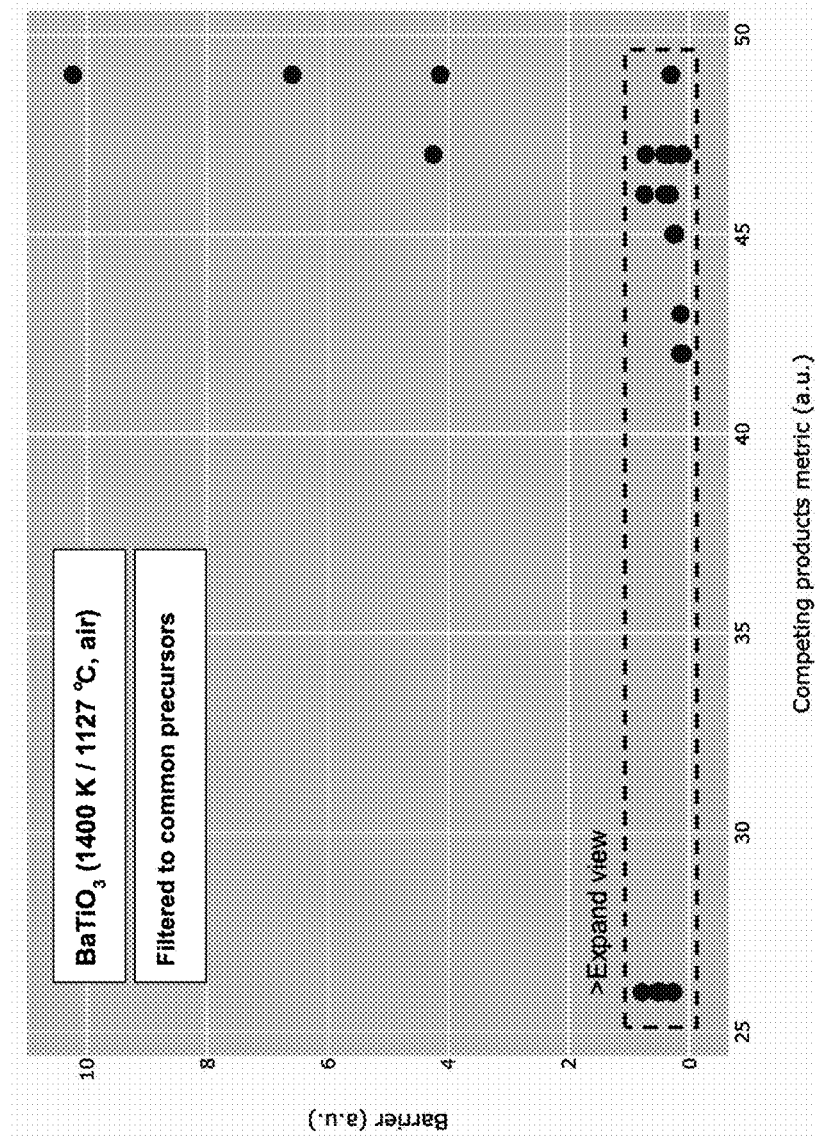
FIG. 9 is an exemplary output for the inorganic synthesis route identifying program for perovskite $BaTiO_3$ synthesis under typical, exemplary thermodynamic conditions from common oxide, carbonate and other carbon-bearing starting materials, where the recommended procedures are those relatively closer to the origin of the plot and points forming or near the pareto frontier, and a display for the option to select and expand the region of interest of the plot is shown, where the expansion is separately viewed in FIG. 10.
Figure 10:
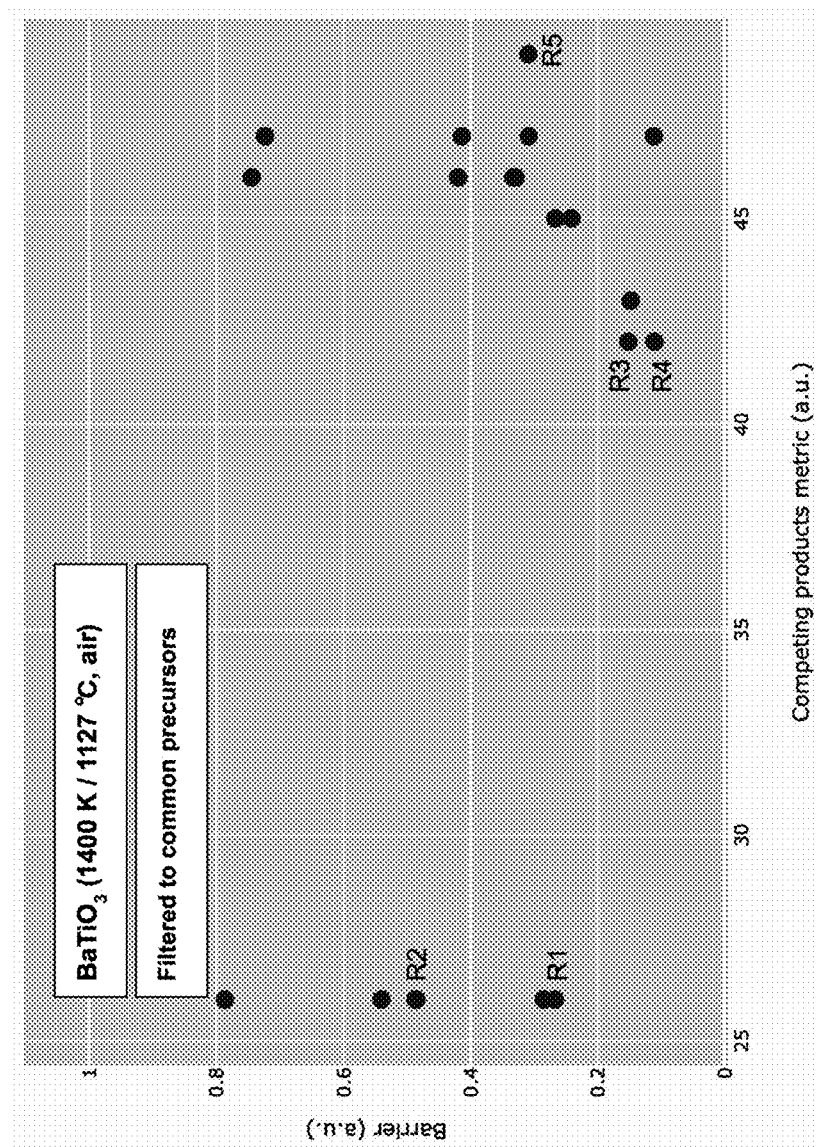
FIG. 10 is the selected region display of the recommendation plot of perovskite $BaTiO_3$ displayed in FIG. 9, where several exemplary reactions are labeled, a list of which is provided in FIG. 16; and where the recommended procedures are those relatively closer to the origin of the plot and points forming or near the pareto frontier.
Figure 11:
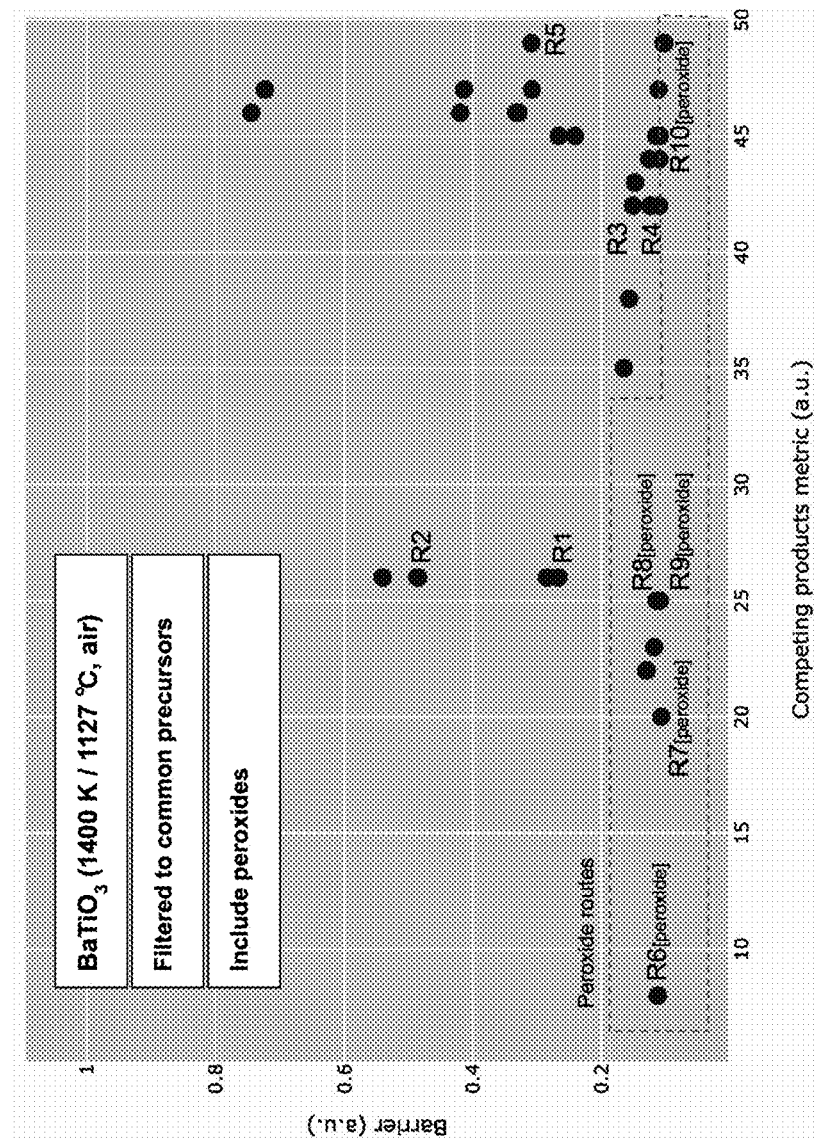
FIG. 11 is an exemplary output for the inorganic synthesis route identifying program for perovskite $BaTiO_3$ synthesis under typical, exemplary thermodynamic conditions from common oxide, carbonate and other carbon-bearing starting materials as well as metal peroxides, where the recommended procedures are those relatively closer to the origin of the plot and points forming or near the pareto frontier; and where several exemplary reactions are labeled, a list of which is provided in FIG. 16.
Figure 12:
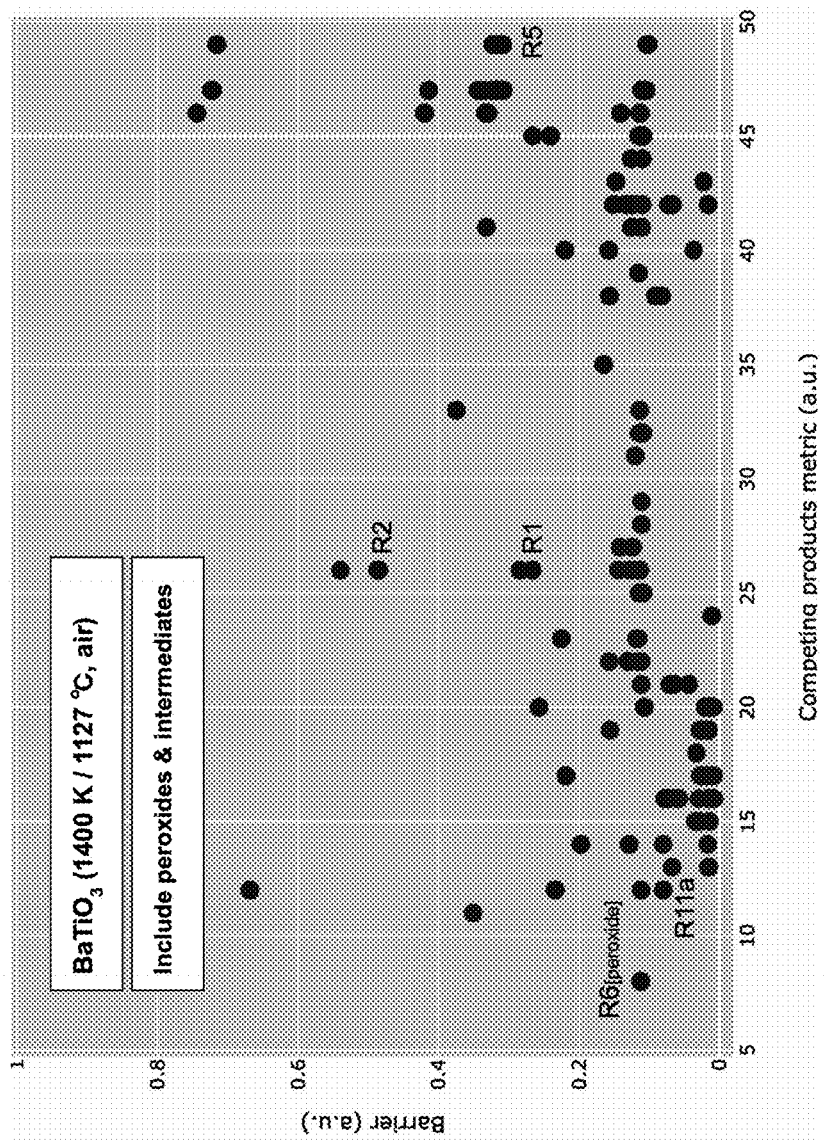
FIG. 12 is an exemplary output for the inorganic synthesis route identifying program for perovskite $BaTiO_3$ synthesis under typical, exemplary thermodynamic conditions from common oxide, carbonate and other carbon-bearing starting materials, metal peroxide starting materials, as well as possible Ba—Ti—O bearing intermediates, where the recommended procedures are those relatively closer to the origin of the plot and points forming or near the pareto frontier; and where several exemplary reactions are labeled, a list of which is provided in FIG. 16.

In the competing phase finder F, a metric is computed that is the number of possible thermodynamically favorable competing phases ($N_{competing}$) for any synthesis reaction directed to the target phase inorganic material β. A viable competing phase requires a thermodynamically favorable reaction energy for its formation from reactants. Hence, from the reactants of a selected reaction for synthesis of the target inorganic material β, the number of possible products, $N_{competing}$ that have viable, negative, reaction energies starting from the same reactants are enumerated, in the manner illustrated in FIG. 3. For consistency, reaction energies for competing phase finding are computed with the same process and conditions used for E1. A relatively larger value of $N_{competing}$ for a given reaction indicates a higher likelihood to yield impurities or other phases when the reaction is carried out, compared to other reactions that have smaller values of $N_{competing}$. Synthesis reactions that minimize the number of possible competing phases to the target inorganic material β are favored relative to others.

Ultimately, the inorganic synthesis identifying program produces a recommendation plot of possible synthesis reactions leading to the target inorganic material β in a recommendation visualizer (G) that can be an interactive recommendation visualizer, as shown in FIG. 1. These visualizations display the nucleation barrier and competition metrics for each synthesis reaction for the target phase, where a relatively smaller value for each indicates a relatively more favorable route. Examples of such recommendation plots and exemplifying reactions are shown in FIGS. 4-28 for the synthesis of various inorganic materials and further explained in the Examples, below. The recommender plots can be interactive, where hovering over a point for a reaction displays information concerning the transformation. As smaller values are desired for the two independent metrics plotted on x and y axes, those reactions near or relatively close to the x-y origin and those forming or near the Pareto frontier of the scatter plot are the relatively more favorable reactions, and hence recommended to be prioritized in synthesis attempts based on the inorganic synthesis identifying program to produce the target inorganic material β. The inorganic synthesis identifying program results can be output as a Pareto optimal subset plot or can be configured to recommend the most viable point or points. The output recommended synthesis can be used as the input to a robotic synthesizer.

Figure 29:
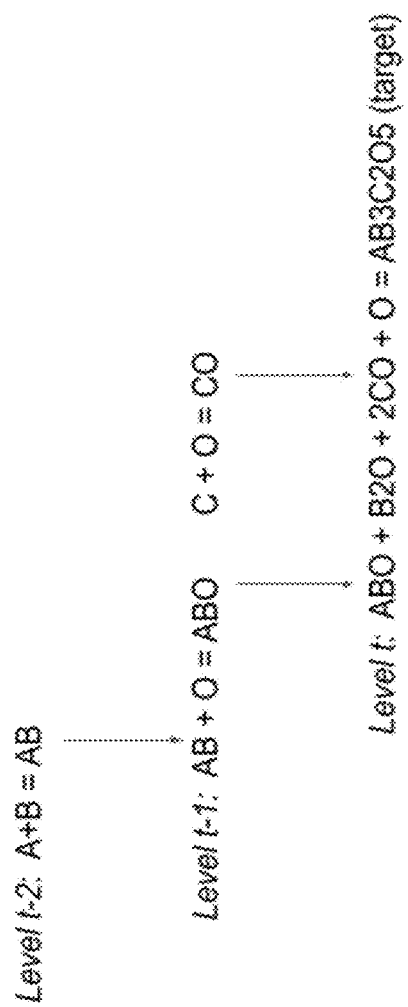
FIG. 29 is a plot of a progression of a multistep synthesis that can be calculated for consideration as a single recommendation where the recommended reactions to intermediate products are determined via a retrosynthetic analysis in addition to the final transformation.

The inorganic synthesis identifying program can be employed recursively to convert a desired reactant combination in a multistep process to yield a target inorganic material β, as shown in FIG. 29. In this manner, where a reactant is not directly or commercially available to prepare the target, the reactant becomes an intermediate in a multistep synthesis. This recursive approach is exemplified as part of Examples 2 and 3.

In other aspects of the invention, cost can be considered in the selection of starting materials/precursors and bias the recommendations from the inorganic synthesis identifying program. Other factors that can be considered to bias the recommendations are to explicitly include or avoid certain reactants, elemental phases, or alloys, and such filters can be input by the user. For example, peroxides or superoxides can be avoided or explicitly included, based on user instruction. System can be instructed to use subclasses of starting materials/precursors, such as, carbonates and nitrates. The program can also bias the recommendation based on the oxidation state of the atoms in the target inorganic material and the reactant(s) from which it is synthesized, for example the recommendation can be where similar oxidation states of reactants and products are favored. The program can be biased for carbothermal synthetic conditions for the preparation of ceramics.

The program can allow the inclusion of catalysts for the synthetic transformations. Unreactive materials towards the reagents that are similar to and/or are epitaxially matching with the target inorganic material can be included for this purpose. Catalysts can be determined by a non-reactivity exhibited by a direct tie-lines between reagent phases and the nucleation agent (catalyst) and the target inorganic material phase and the nucleation agent. Co-precipitation with the target inorganic material can be allowed where purity of the target inorganic material is not a requirement.

The systems, components and methods described above can be realized in hardware or a combination of hardware and software and can be realized primarily in a centralized fashion in one processing system while some elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Hardware arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a hard disk drive (HDD), a solid-state drive (SSD), a read-only memory (ROM), an erasable programmable read-only memory, a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Generally, "module," as used herein, includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module may be implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Various aspects of the present disclosure are further illustrated with respect to the following Examples. It is to be understood that these Examples are provided to illustrate specific embodiments of the present disclosure and should not be construed as limiting the scope of the present disclosure in or to any particular aspect.

The headings (such as "Background" and "Summary") and sub-headings used herein are intended only for general organization of topics within the present disclosure and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes examples, the true scope of the disclosure should not be so limited since other modifications will become apparent to the skilled practitioner upon a study of the specification and the following claims. Reference herein to one aspect, or various aspects means that a feature, structure, or characteristic described in connection with an embodiment or system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

Various aspects of the present disclosure are further illustrated with respect to the following Examples. Examples 1 to 3 are directed to widely studied inorganic compounds where multiple routes to the same target have been reported in the literature, and hence a detailed validation of the described recommender system can be carried out. Examples 4 to 10, are directed to successful generalization of the recommender system to a diverse array of inorganic compounds reported to be synthesized using various solid-state routes in the literature. It is to be understood that these Examples are provided to illustrate specific embodiments of the present disclosure and should not be construed as limiting the scope of the present disclosure in or to any particular aspect.

Example 1 Recommendation for Synthesis of $LiCoO_2$

High-temperature (layered) form of $LiCoO_2$ (HT-LCO) is a widely used cathode material for Li-ion batteries. Reports show HT-LCO can be synthesized with $Li_2CO_3$ as Li source, and Co, CoO, $Co_3O_4$ or $CoCO_3$ as Co source (Mizushima et al. 1981, Antolini et al. 1995, Feretti 2004, Lundblad et al. 1997, and Carewska et al. 1995). These routes first lead to formation of $Co_3O_4$, or CoO, depending on the temperature, which then reacts with the Li precursor (Feretti 2004). A peroxide route based on $Li_2O_2$ and CoO has also been reported to yield HT-LCO (Johnson et al. 1958). The synthesis route recommender system, disclosed herein, recovers and agrees with all these viable routes reported in the literature; where, as shown in FIGS. 5 through 8, identify them as favorable routes under relevant thermodynamic conditions and precursor selections, validating the utility of the synthesis route recommendation system disclosed herein.

Example 2 Recommendation for Synthesis of $BaTiO_3$ $BaTiO_3$ is a widely studied ferroelectric material with numerous applications in industry. High-temperature reactions, generally between 800° C. and 1300° C., using common precursors, such as $BaCO_3$ or BaO as the Ba source, and $TiO_2$ are conventional methods to make tetragonal perovskite $BaTiO_3$ (Stojanovic et al. 2005, Cournil et al. 1979, Buscaglia et al. 2005, Beauger et al. 1983, and Lee et al. 2011). Use of $BaO_2$, peroxide, as the Ba source has been reported (Komarov et al. 1996, Licheri et al. 2007, and Larson et al. 1999). The synthesis route recommender system recovers and agrees with all these viable routes reported in the literature, as can be seen in FIGS. 9 through 12, and FIG. 16, identifying these methods as favorable routes under relevant thermodynamic conditions and precursor selections; validating the utility of the synthesis route recommendation system disclosed herein.

Figure 13:
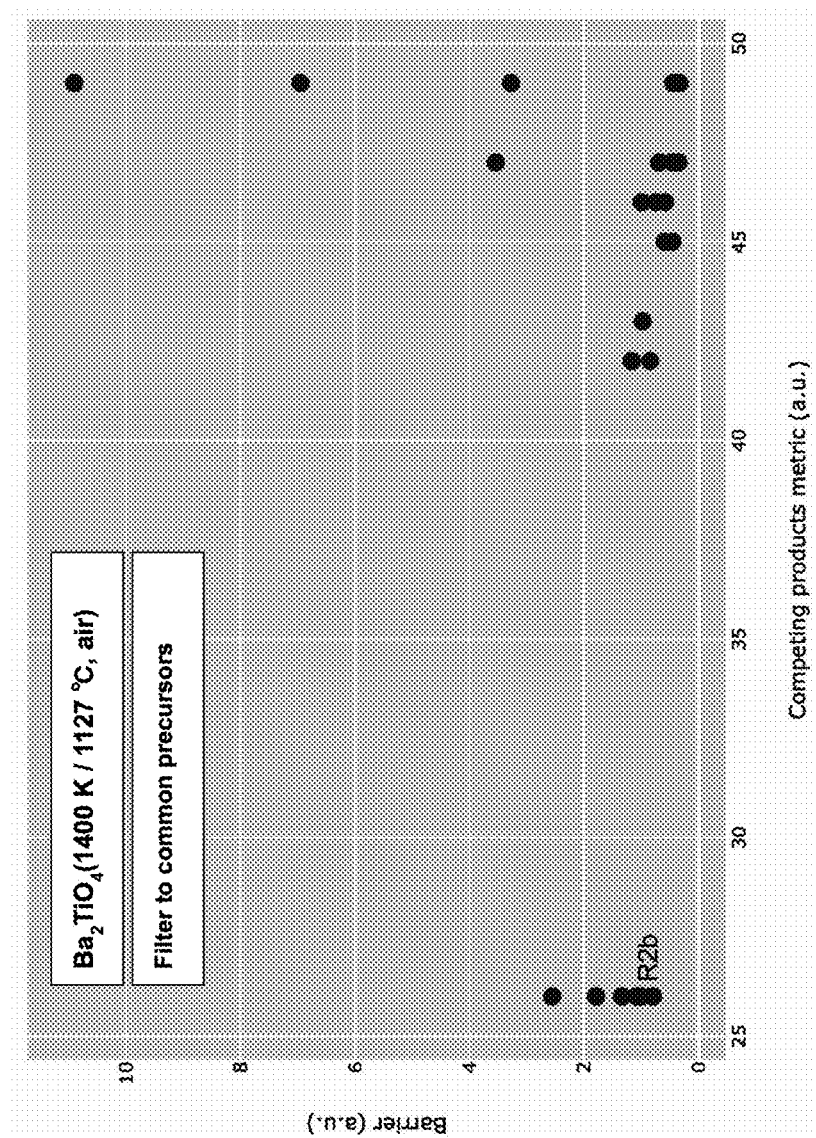
FIG. 13 is an exemplary output for the inorganic synthesis route identifying program for $Ba_2TiO_4$ synthesis under typical, exemplary thermodynamic conditions from common oxide, carbonate and other carbon-bearing starting materials, where the recommended procedures are those relatively closer to the origin of the plot and points forming or near the pareto frontier; where the reaction labeled is listed in FIG. 16
Figure 14:
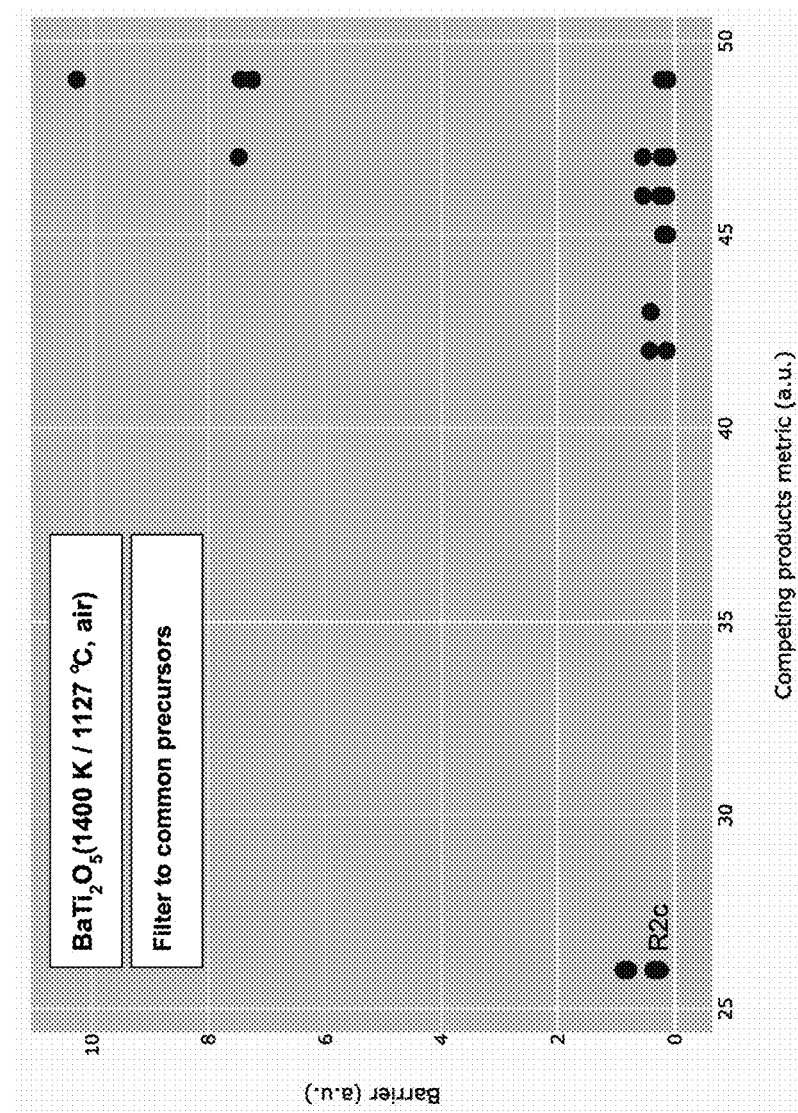
FIG. 14 is an exemplary output for the inorganic synthesis route identifying program for $BaTi_2O_5$ synthesis under typical, exemplary thermodynamic conditions from common oxide, carbonate and other carbon-bearing starting materials, where the recommended procedures are those relatively closer to the origin of the plot and points forming or near the pareto frontier; where the reaction labeled is listed in FIG. 16
Figure 15:
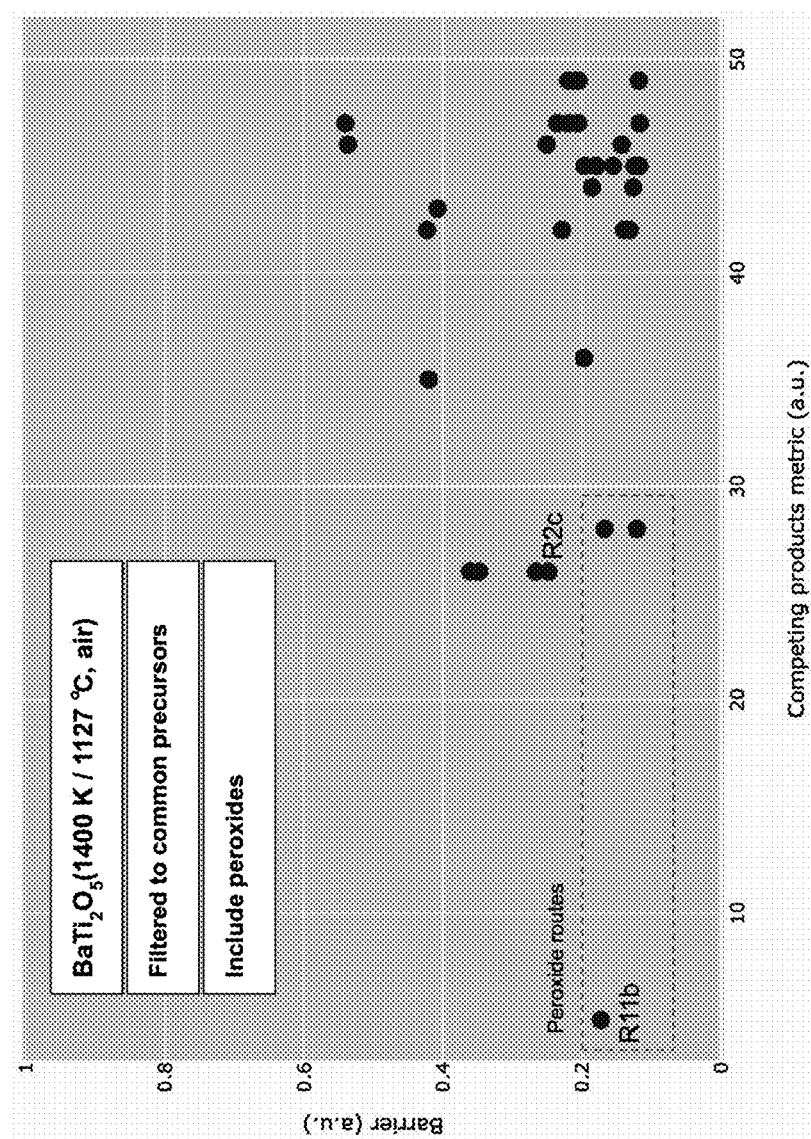
FIG. 15 is an exemplary output for the inorganic synthesis route identifying program for $BaTi_2O_5$ synthesis under typical, exemplary thermodynamic conditions from common oxide, carbonate and other carbon-bearing starting materials as well as metal peroxide starting materials, where the recommended procedures are those closer to the origin of the plot and points forming or near the pareto frontier; where the reaction labeled is listed in FIG. 16
Figure 17:
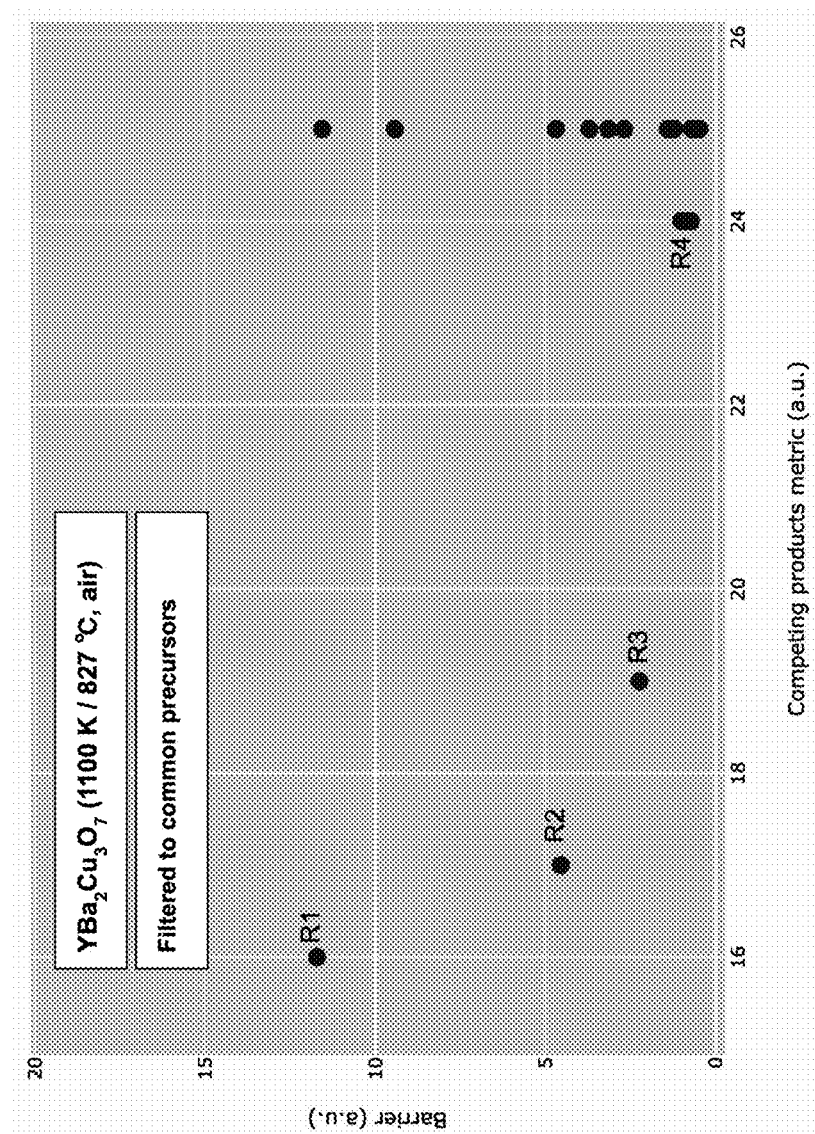
FIG. 17 is an exemplary output for the inorganic synthesis route identifying program for $YBa_2Cu_3O_7$ synthesis under typical, exemplary thermodynamic conditions from common oxide, carbonate and other carbon-bearing starting materials, where the recommended procedures are those relatively closer to the origin of the plot and points forming or near the pareto frontier; where several exemplary reactions are labeled, a list of which is provided in FIG. 21.
Figure 18:
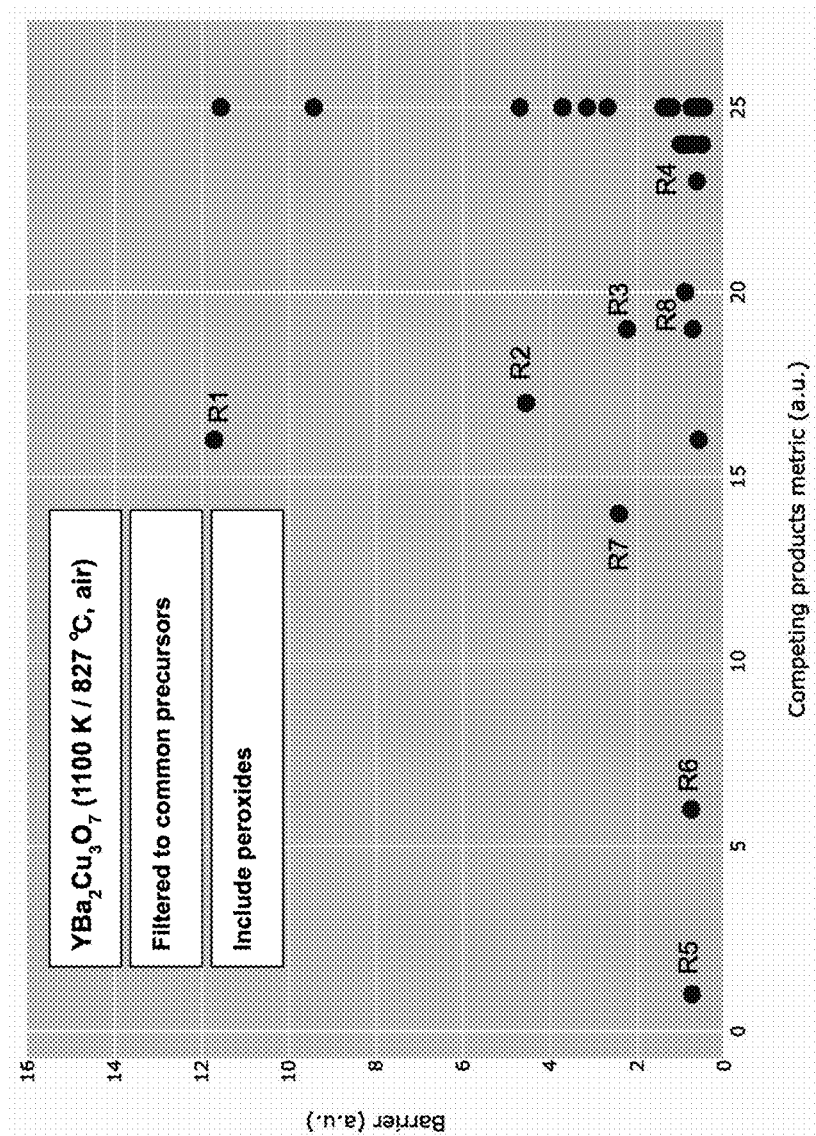
FIG. 18 is an exemplary output for the inorganic synthesis route identifying program for $YBa_2Cu_3O_7$ synthesis under typical, exemplary thermodynamic conditions from common oxide, carbonate and other carbon-bearing starting materials as well as metal peroxides, where the recommended procedures are those relatively closer to the origin of the plot and points forming or near the pareto frontier, where several exemplary reactions are labeled, a list of which is provided in FIG. 21.

An inorganic multi-step synthesis analysis case study enabled by the synthesis route recommender system considers that the conventional synthesis of $BaTiO_3$ from $BaCO_3$ and $TiO_2$ yields side products, such as $Ba_2TiO_4$ and $BaTi_2O_5$. (Lotnyk et al. 2006, Rossel et al. 2004, Lee et al. 2011, Beauger et al. 1983, Buscaglia et al. 2005, and Pfaff 1991) The recommender plots of these phases recover $BaCO_3$ and $TiO_2$ as highly favorable for the formation of both intermediates, in agreement with these experimental observations, as shown in FIGS. 13 through 15. Multiple sequential routes from a multi-step analysis can help circumvent the formation of such impurities, by deliberately controlling their presence in synthesis reactions. First, a comprehensive recommender plot can be obtained by allowing intermediates, those materials containing Ba, Ti, O and/or C, which are not necessarily known as common precursors as reactants in reactions. In such a plot for $BaTiO_3$, FIG. 12, a route (R11a) with BaO and $BaTi_2O_5$ appears as highly favorable. A peroxide-including recommender plot for $BaTi_2O_5$, FIG. 15, yields a highly favored reaction (R11b). Hence these two reactions, R11a and R11b, allow construction of a two-step targeted synthesis strategy for $BaTiO_3$. As above, studies on the synthesis of $BaTiO_3$ from $BaCO_3$ and $TiO_2$ report $BaTi_2O_5$ as an intermediate phase, and its conversion to $BaTiO_3$ upon favorable conditions, confirming the plausibility of multi-step analysis enabled by the recommender system.

Example 3 Recommendation for Synthesis of $YBa_2Cu_3O_7$ $YBa_2Cu_3O_7$ (YBCO) is a widely studied high-temperature superconducting cuprate. High temperature reactions between common precursors $Y_2O_3$, CuO and $BaCO_3$ or $BaO$ are the conventional routes to its solid-state synthesis. (Wu et al. 1987, Ruckenstein et al. 1989) Use of Cu metal as the Cu-source and peroxide $BaO_2$ as the Ba-source in a combustion type route has been reported to yield YBCO. (Lebrat et al. 1992) Use of $BaO_2$ with CuO and $Y_2O_3$ also yields YBCO (Hepp et al. 1998 and Costa et al. 1987). The use of peroxide $BaO_2$ and $Cu_2O$ is reported to be a highly favored route, yielding phase pure YBCO in a single step with no carbonate impurities. (Kao 1987, Kao et al. 1991) The synthesis route recommender system recovers and agrees with these viable routes reported in the literature, as indicated in FIGS. 17 to 19, and FIG. 21, identifying these as favorable routes under relevant thermodynamic conditions and precursor selections, validating the utility of synthesis route recommendation system disclosed herein.

Figure 19:
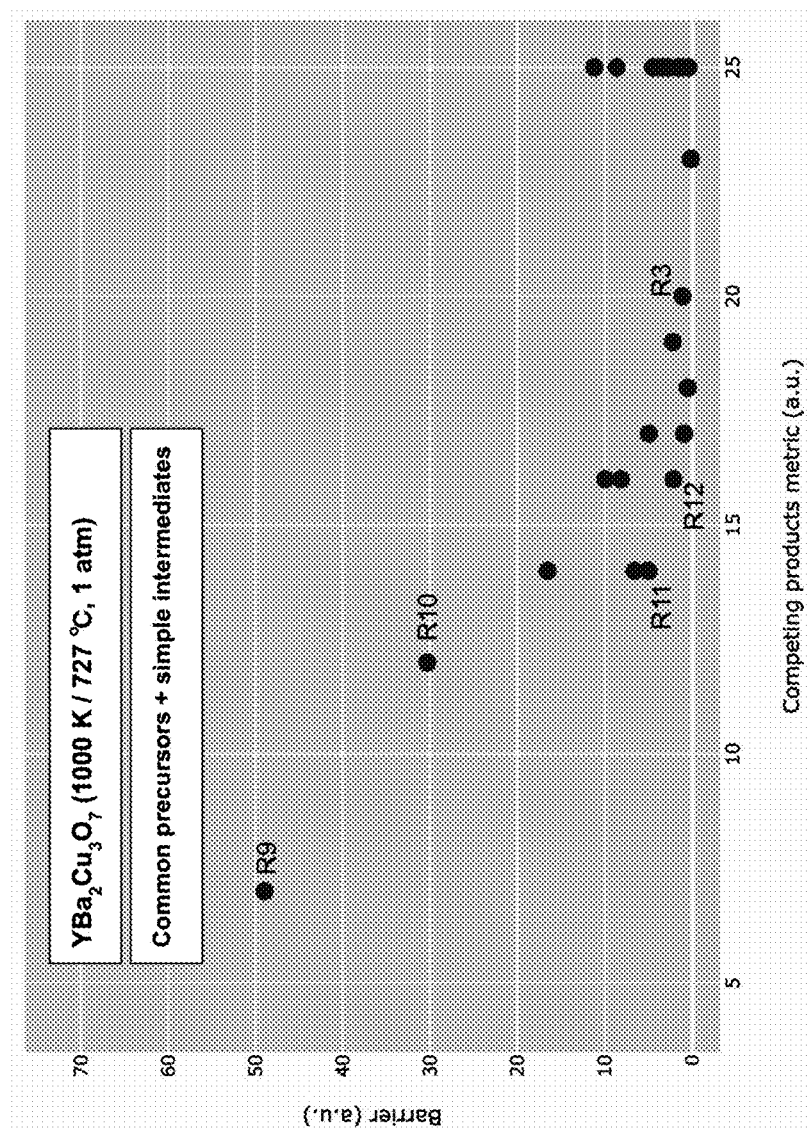
FIG. 19 is an exemplary output for the inorganic synthesis route identifying program for $YBa_2Cu_3O_7$ synthesis under typical, exemplary thermodynamic conditions from common oxide, carbonate and other carbon-bearing starting materials as well as possible ternary intermediates in Y—Ba—Cu—O system, where the recommended procedures are those relatively closer to the origin of the plot and points forming or near the pareto frontier; and where several exemplary reactions are labeled, a list of which is provided in FIG. 21.
Figure 20:
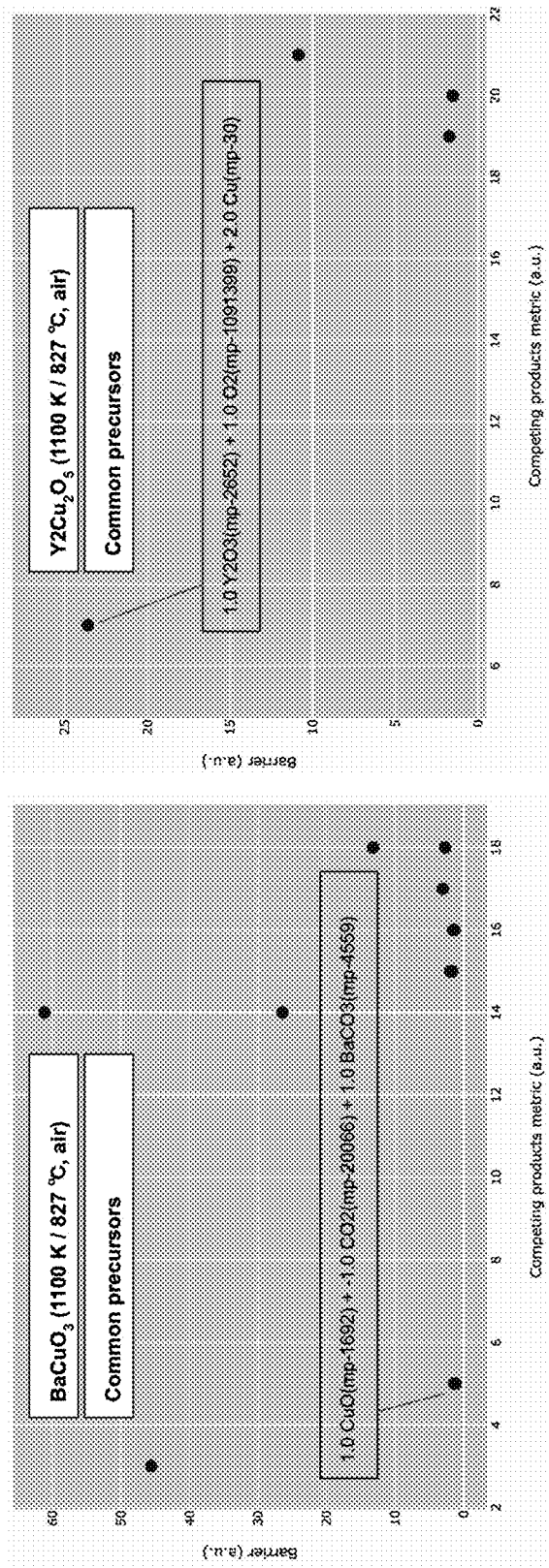
FIG. 20 shows exemplary outputs for the inorganic synthesis route identifying program for $BaCuO_2$ and $Y_2Cu_2O_5$ synthesis under typical, exemplary thermodynamic conditions from common oxide, carbonate and other carbon-bearing starting materials, where the recommended procedures are those relatively closer to the origins of each plot and points forming or near the pareto frontiers.
Figure 22:
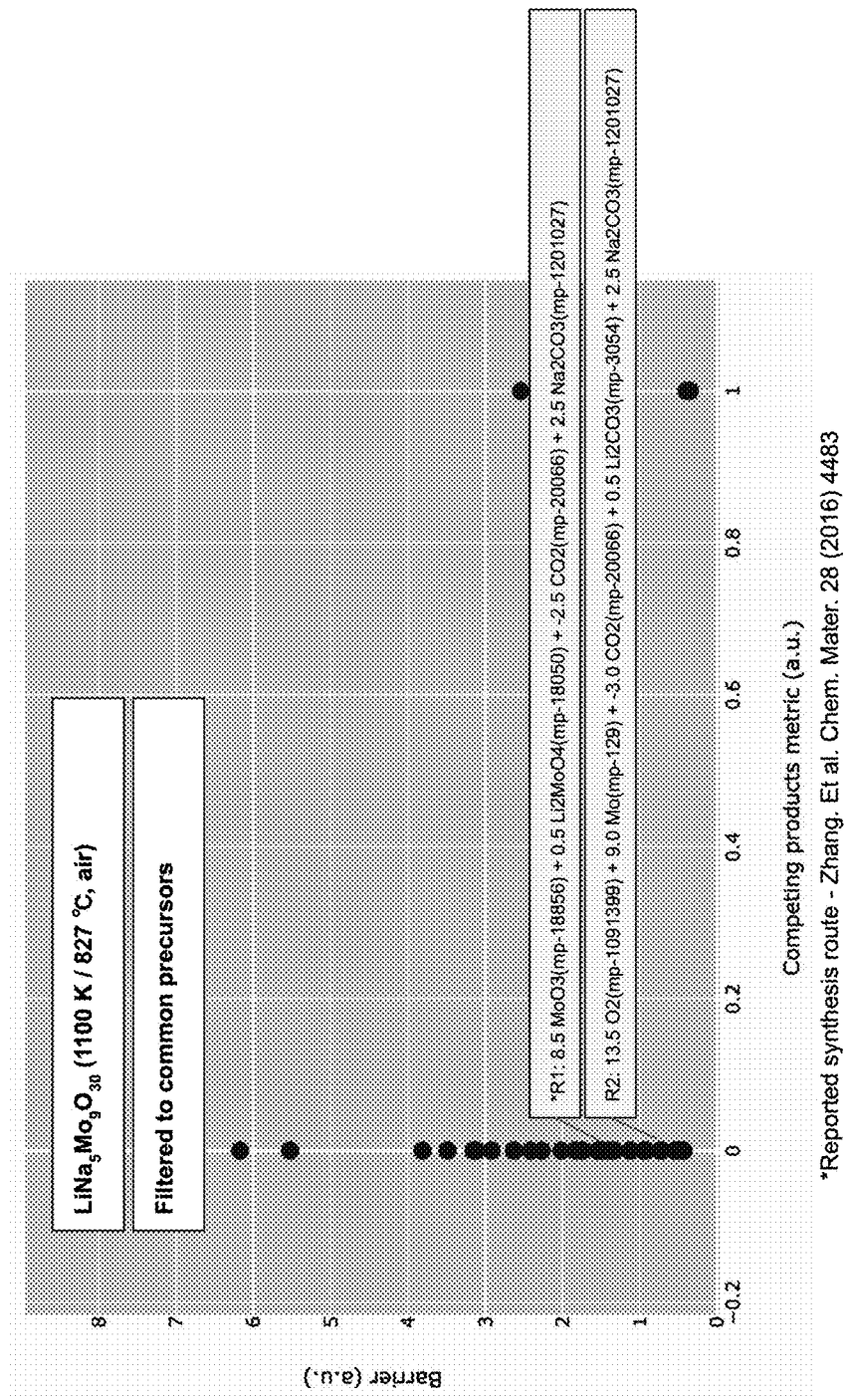
FIG. 22 is an exemplary output for the inorganic synthesis route identifying program for $LiNa_5Mo_9O_{30}$ synthesis under typical, exemplary thermodynamic conditions from common oxide, carbonate and other carbon-bearing starting materials, where the recommended procedures are those relatively closer to the origin of the plot and points forming or near the pareto frontier.
Figure 23:
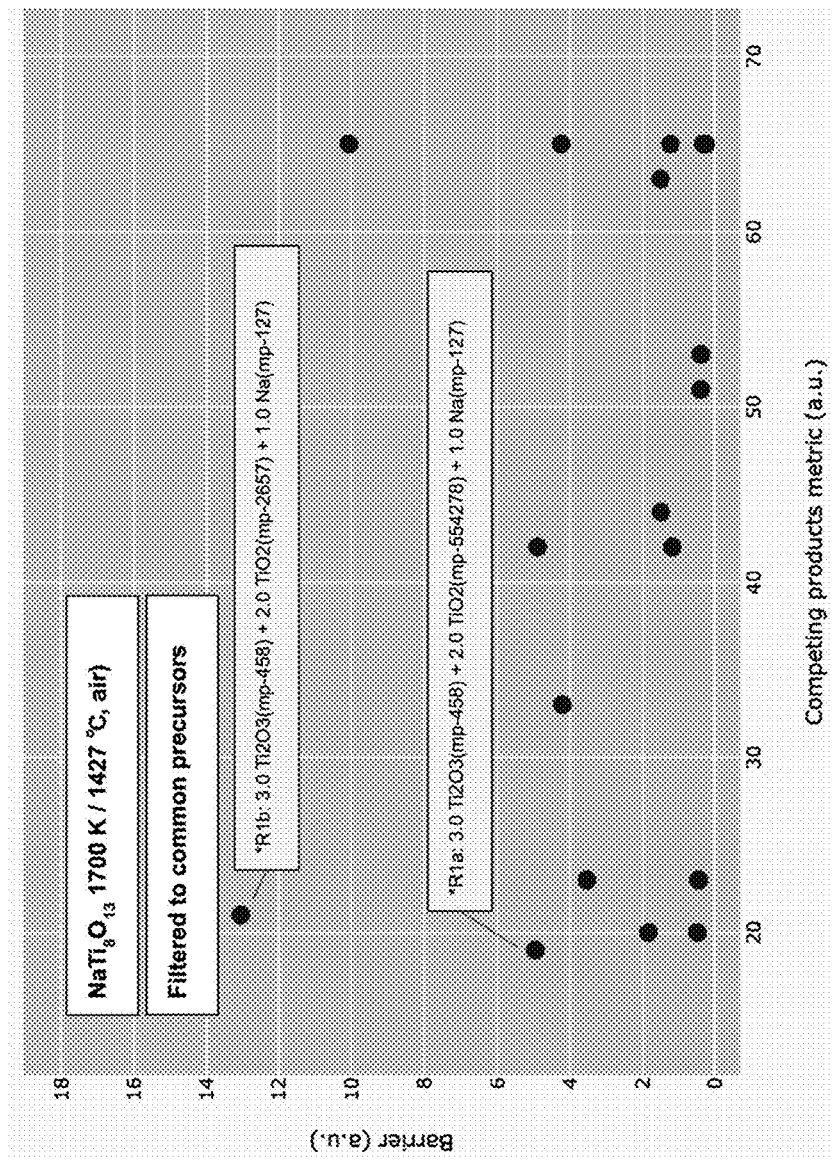
FIG. 23 is an exemplary output for the inorganic synthesis route identifying program for $NaTi_8O_{13}$ synthesis under typical, exemplary thermodynamic conditions from common metal/metal oxide starting materials, where the recommended procedures are those relatively closer to the origin of the plot and points forming or near the pareto frontier.
Figure 24:
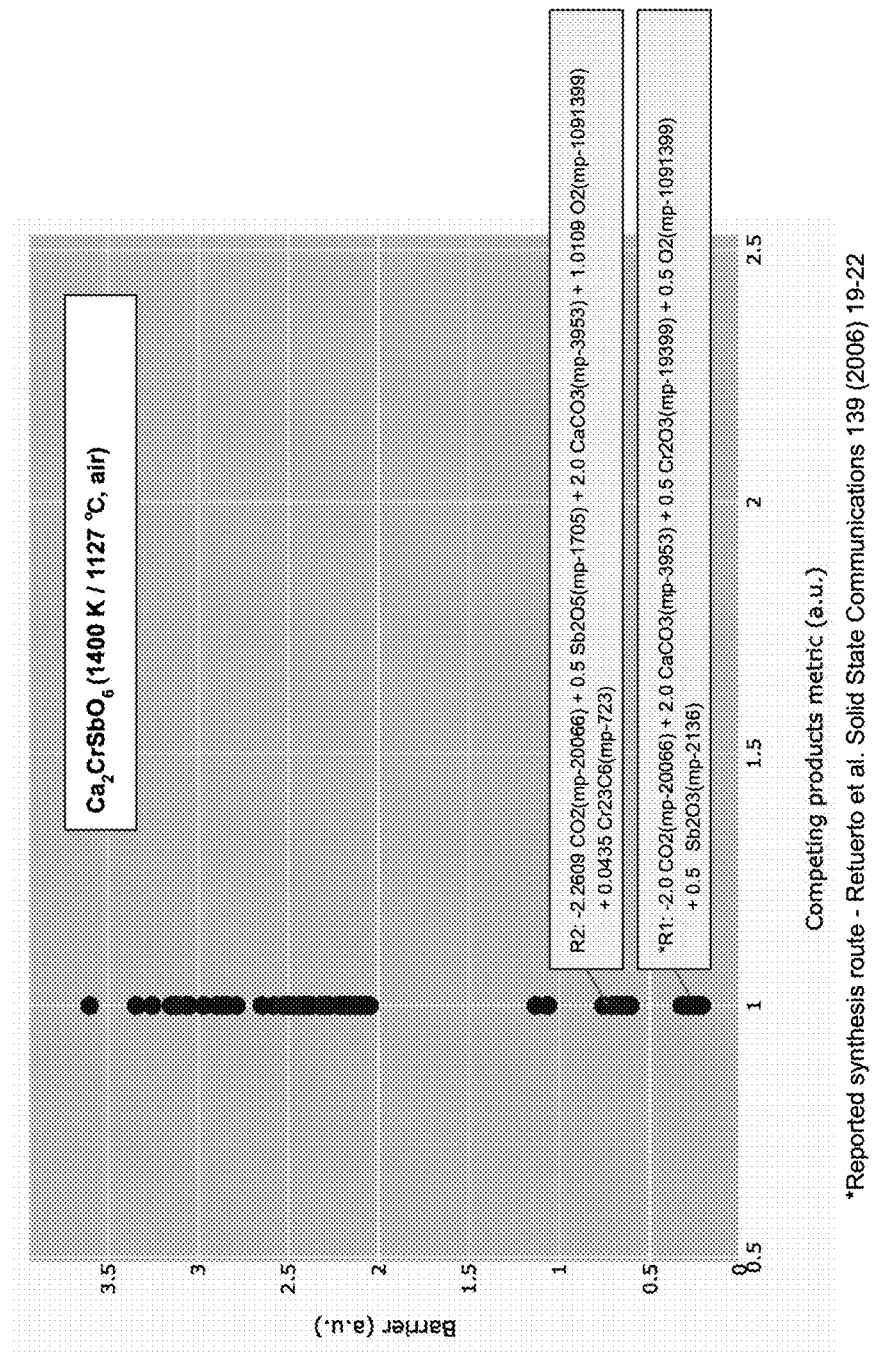
FIG. 24 is an exemplary output for the inorganic synthesis route identifying program for $Ca_2CrSbO_6$ synthesis under typical, exemplary thermodynamic conditions from common metal/metal oxide and carbonate starting materials, where the recommended procedures are those relatively closer to the origin of the plot and points forming or near the pareto frontier.
Figure 25:
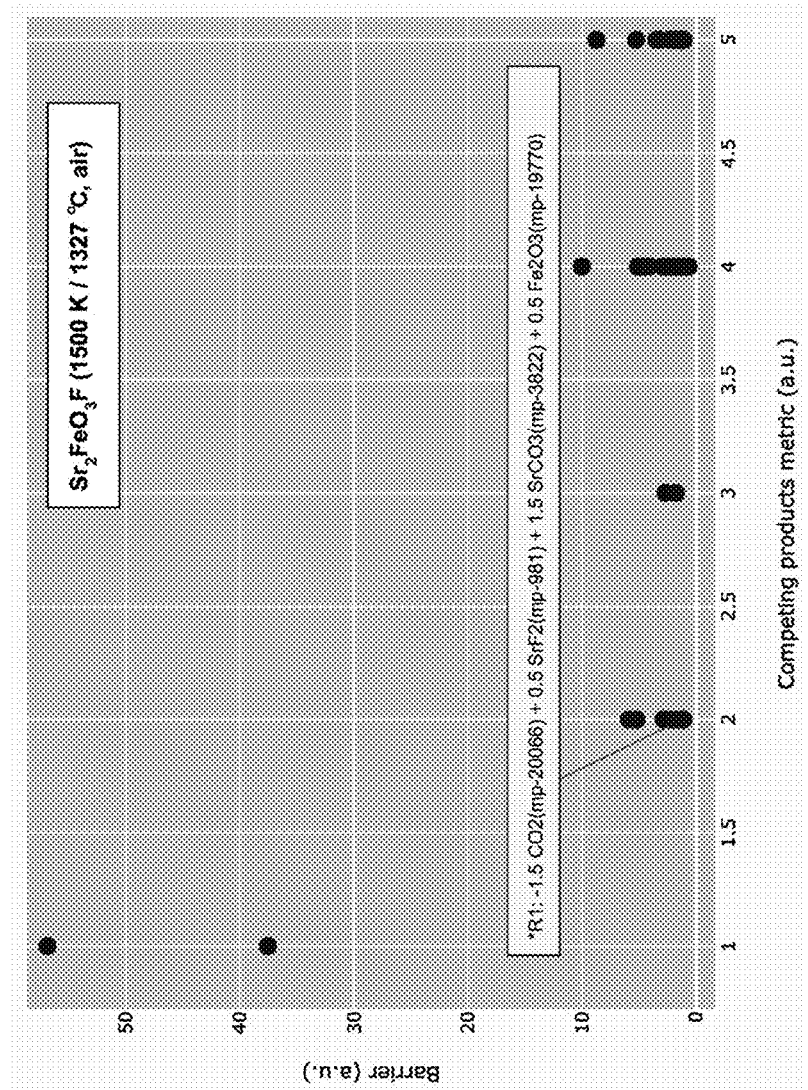
FIG. 25 is an exemplary output for the inorganic synthesis route identifying program for $Sr_2FeO_3F$ synthesis under typical, exemplary thermodynamic conditions from common metal, metal oxide/fluoride/carbonate starting materials, where the recommended procedures are those relatively closer to the origin of the plot and points forming or near the pareto frontier.
Figure 26:
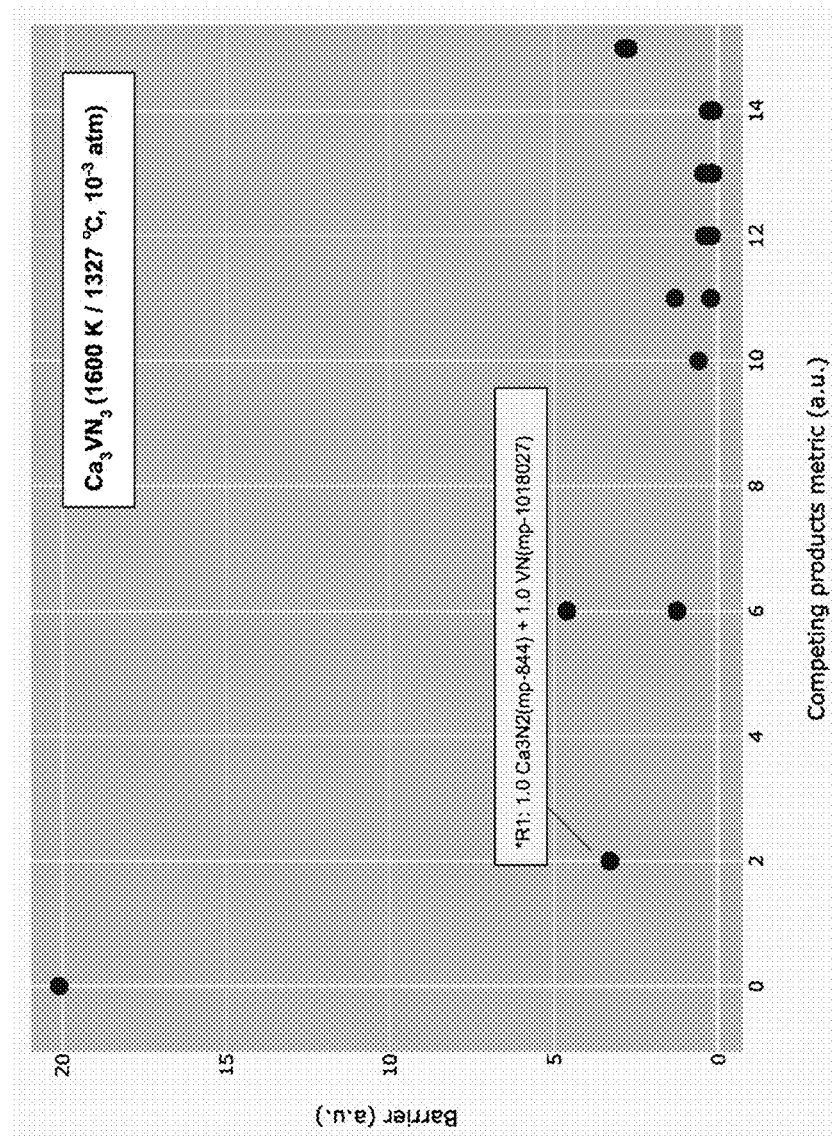
FIG. 26 is an exemplary output for the inorganic synthesis route identifying program for $Ca_3VN_3$ synthesis under typical, exemplary thermodynamic conditions from metal and metal nitride starting materials, where the recommended procedures are those relatively closer to the origin of the plot and points forming or near the pareto frontier.
Figure 27:
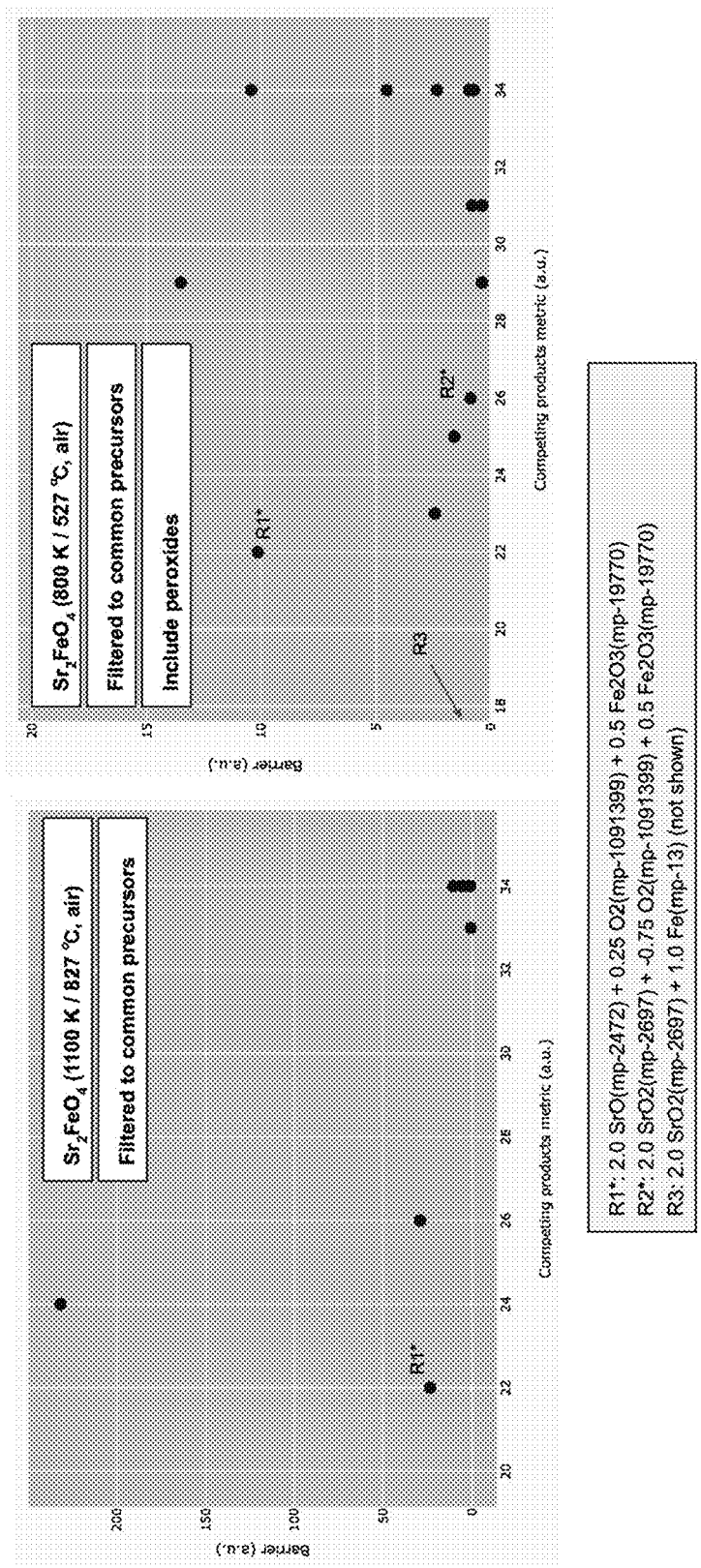
FIG. 27 shows exemplary outputs for the inorganic synthesis route identifying program for $Sr_2FeO_4$ synthesis under typical, exemplary thermodynamic conditions from common metal and metal oxide starting materials as well as peroxide starting materials, where the recommended procedures are those relatively closer to the origins of the plots and points forming or near the pareto frontiers.
Figure 28:
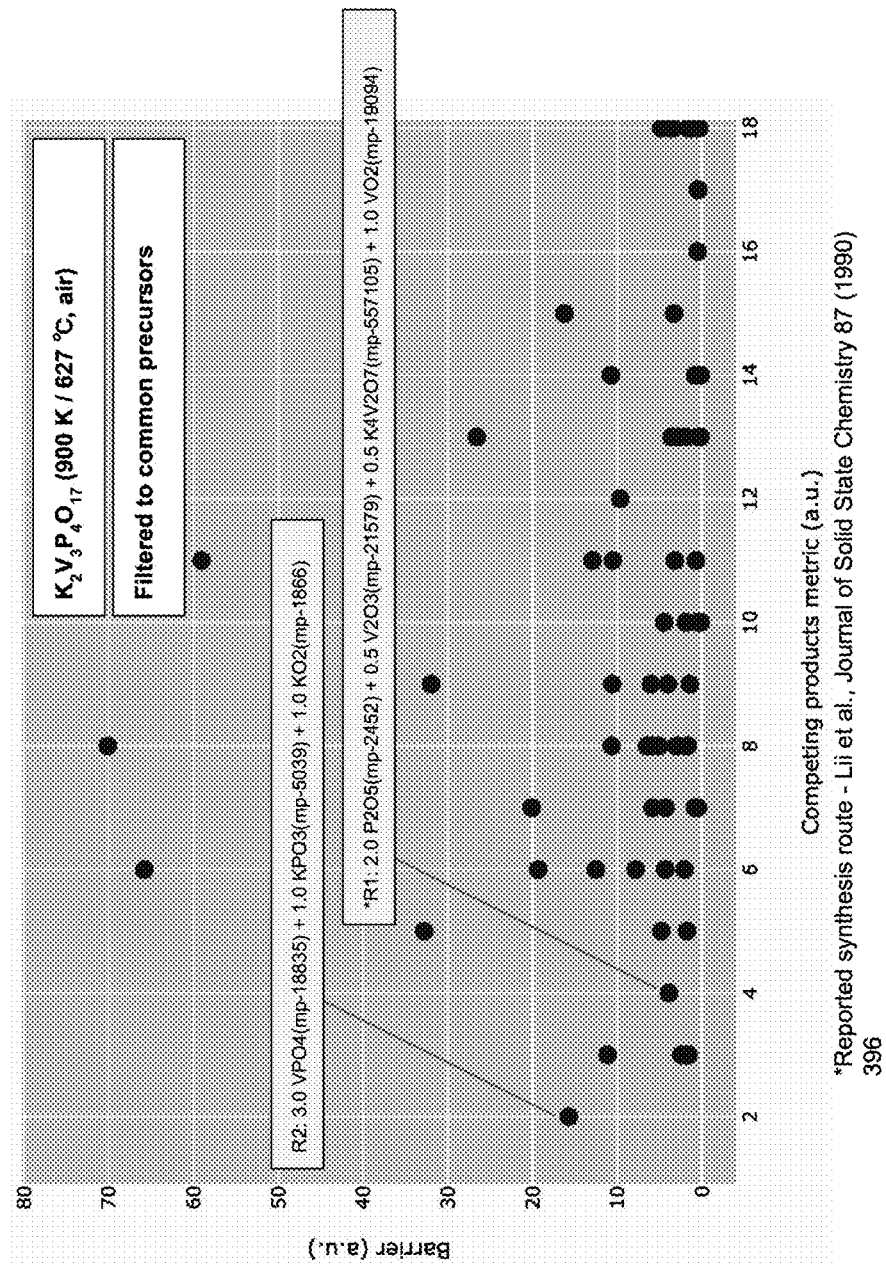
FIG. 28 is an exemplary output for the inorganic synthesis route identifying program for $K_2V_3P_4O_{17}$ synthesis under typical, exemplary thermodynamic conditions from common starting materials in this system, where the recommended procedures are those relatively closer to the origin of the plot and points forming or near the pareto frontier.

An inorganic multi-step synthesis analysis case study enabled by the synthesis route recommender system considers that $Y_2Cu_2O_5$ and $BaCuO_2$ are two common intermediates in this system (Peterson et al. 1991, Ruckenstein et al. 1989, Cogdell et al. 1995) that may be synthesized from common precursors separately and reacted under $O_2$-flow to yield YBCO (FIG. 20). A recommender plot for YBCO under relevant thermodynamic conditions shows a reaction with these intermediates as precursors is favorable (FIG. 19). To summarize, multi-step retrosynthetic routes (FIG. 21, R10-R12) that are plausible (in light of the above cited literature data) can be constructed where the initial step pertains to synthesis of one or both of these intermediates, and a second step leading to formation of YBCO using the product of the first reaction and common precursors (if needed).

Example 4 Recommendation for Synthesis of $LiNa_5Mo_9O_{30}$

Solid-state synthesis route for the compound $LiNa_5Mo_9O_{30}$ reported by Zhang et al. 2016 is shown by the recommender system (FIG. 22) as relatively favorable under relevant thermodynamic conditions and precursor selections.

Example 5 Recommendation for Synthesis of $NaTi_8O_{13}$

Solid-state synthesis route for the compound $NaTi_8O_{13}$ reported by Akimoto et al. 1991 is shown by the recommender system (FIG. 23) as relatively favorable under relevant thermodynamic conditions and precursor selections.

Example 6 Recommendation for Synthesis of $Ca_2CrSbO_6$

Solid-state synthesis route for the compound $Ca_2CrSbO_6$ reported by Retuerto et al. 2006 is shown by the recommender system (FIG. 24) as relatively favorable under relevant thermodynamic conditions and precursor selections.

Example 7 Recommendation for Synthesis of $Sr_2FeO_3F$

Solid-state synthesis route for the compound $Sr_2FeO_3F$ reported by Galasso and Darby 1963 is shown by the recommender system (FIG. 25) as relatively favorable under relevant thermodynamic conditions and precursor selections.

Example 8 Recommendation for Synthesis of $Ca_3VN_3$

Solid-state synthesis route for the compound $Ca_3VN_3$ reported by Vennos et al. 1992 is shown by the recommender system (FIG. 26) as relatively favorable under relevant thermodynamic conditions and precursor selections.

Example 9 Recommendation for Synthesis of $Sr_2FeO_4$

Solid-state synthesis routes for the compound $Sr_2FeO_4$ reported by Dann et al. 1991 and Thompson et al. 2013 are shown by the recommender system (FIG. 27) as relatively favorable under relevant thermodynamic conditions and precursor selections.

Example 10 Recommendation for Synthesis of $K_2V_3P_4O_{17}$

Solid-state synthesis route for the compound $K_2V_3P_4O_{17}$ reported by Lii et al. 1990 is shown by the recommender system (FIG. 28) as relatively favorable under relevant thermodynamic conditions and precursor selections.

REFERENCES

Akimoto et al., *Journal of Solid State Chemistry* 90 (1991) 147.

Antolini et al., *Journal of Solid State Chemistry* 117 (1995) 1.
Beauger et al., *Mater. Sci.* 18 (1983) 3041.
Beauger et al., *Mater. Sci.* 18 (1983) 3543.
Buscaglia et al., *J. Am. Ceram. Soc.*, 88 (2005) 2374.
Carewska et al., *Thermochimica Acta* 269; 370 (1995) 491.
Cogdell et al., *Journal of Chemical Education* 72 (1995) 840.
Costa et al., *J. Crystal Growth* 85 (1987) 623.
Cournil et al., *Oxidation of Metals* 13 (1979) 77.
Dann et al., *Journal of Solid State Chemistry* 92 (1991) 237.
Ferretti, *Solid State Ionics* 170 (2004) 159.
Galasso et al., *J. Phys. Chem.* 67 (1963) 1451.
Hepp et al., *Mat. Res. Bull.* 23 (1988) 693
Johnson et al., *J. Phys. Chem. Solids* 7 (1958) 1.
Kao et al., *Materials Letters* 11 (1991) 91.
Kao, *Materials Letters* 6 (1987) 53.
Komarov et al., *Polyhedron* 15 (1996) 1349.
Larson et al. *Powder Diffr.* 14 (1999) 111.
Lebrat et al., *Combust. Sci. and Tech.* 88 (1992) 177.
Lee et al., *Jpn. J. Appl. Phys.* 50 (2011) 091502.
Licheri et al., *Journal of the European Ceramic Society* 27 (2007) 2245.
Lii et al., *Journal of Solid State Chemistry* 87 (1990) 396.
Lotnyk et al., *Solid State Ionics* 177 (2006) 429.
Lundblad et al., *Solid State Ionics* 96 (1997) 173.
Mizushima et al., *Solid State Ionics* 3-4 (1981) 171.
Peterson et al., *J. Mater. Res.* 6 (1991) 11.
Pfaff, *Journal of Materials Science* Letters 10 (1991) 1059.
Retuerto et al. *Solid State Communications* 139 (2006) 19.
Rossel et al. *Anal Bioanal. Chem.* (2004) 380: 157.
Ruckenstein et al., *J. Mater. Res* 4 (1989) 267.
Stojanovic et al. *Journal of the European Ceramic Society* 25 (2005) 1985.
Thompson et al. U.S. Pat. No. 8,372,441B2 (2013).
Vennos et al., *Journal of Solid State Chemistry* 98 (1992) 318.
Wu et al., *Phys. Rev. Lett.* 58 (1987) 958.
Zhang et al., *Chem. Mater.* 28 (2016) 4483.

What is claimed is:

1. A synthesis route recommendation engine, comprising:
an input device for receiving and selecting a target inorganic material, one or more arguments on thermodynamic conditions, and one or more starting material or precursor subclasses;
one or more processors;
a memory communicably coupled to the one or more processors for storing computed data and data acquired from one or more structural and thermodynamic material databases of a remote computer;
a synthesis reaction enumerator module including instructions that, when executed by the one or more processors, cause the one or more processors to (1) enumerate a plurality of possible synthetic reactions leading to the target inorganic material from data acquired from the structural and thermodynamic material databases and (2) store a synthesis reaction database to the memory;
a nucleation estimator module including instructions that, when executed by the one or more processors, cause the one or more processors to (1) compute a reaction energy under user-specified or a set of default thermodynamic conditions and determine a viable subset of reactions, compute similarity values and identify epitaxially matching facets for a plurality of reactants and the target inorganic material and (2) generate and store a nucleation barrier metric for each synthetic reaction of the viable subset of reactions;
a competition module including instructions that, when executed by the one or more processors, cause the one or more processors to (1) compute a number of possible thermodynamically competing phases and (2) generate and store a competition metric for each synthetic reaction of the viable subset of reactions; and
a recommendation visualizer module including instructions that, when executed by the one or more processors, cause the one or more processors to generate a recommendation plot displaying the nucleation barrier metric and the competition metric for each of the viable subset of reactions and store data of the recommendation plot in a human and/or machine-readable file.

2. The synthesis route recommendation engine according to claim 1, wherein the input device is a user interface configured to receive an input from a user or an output from a routine in the one or more processors.

3. The synthesis route recommendation engine according to claim 1, wherein the one or more materials databases of a remote computer provide tabulated and retrievable empirical data or first-principle computational structural data and thermodynamic data, wherein the computational structural and thermodynamic data are obtained from Materials Project, Open Quantum Materials Database, or AFLOW database, or a first-principle computational database generated remotely or within at least one of the processors.

4. The synthesis route recommendation engine according to claim 1, wherein the synthesis reaction enumerator module calculates balanced stoichiometric reactions to the target inorganic material from all of the reactants available from the structural and thermodynamic materials databases.

5. The synthesis route recommendation engine according to claim 1, wherein the nucleation estimator module computes a reaction energy for each of the synthesis reactions stored in the synthesis reaction database using thermochemical data obtained from one or more of the structural and thermodynamic materials databases under the user-specified or the default thermodynamic conditions, and stores the viable subset of reactions with favorable values of the reaction energy in the synthesis reaction database.

6. The synthesis route recommendation engine according to claim 1, wherein the nucleation estimator module computes the similarity values between each of the reactants and the target inorganic material, obtained directly from a similarity measure or from an inverse relationship with a relative Euclidean or a non-Euclidean distance, measured in a high-dimensional representation space of materials derived from crystal structure data of the reactants and the target inorganic material, for each of the viable subset of reactions stored in the synthesis reaction database.

7. The synthesis route recommendation engine according to claim 1, wherein the nucleation estimator module computes epitaxial matching quantities as minimal matching areas or derived scores for each of the reactant and the target material; for each of the viable subset of reactions in the synthesis reaction database.

8. The synthesis route recommendation engine according to claim 1, wherein the nucleation estimator module computes a nucleation barrier related metric for each viable synthetic reaction from the reaction energy, the similarity values and the epitaxial matching facets.

9. A computational method to determine an optimal solid-state synthetic method for synthesis of an inorganic material, comprising receiving a target inorganic material from a user or from an output from a program in a processor;

querying structural data and thermodynamic data for the target inorganic material from any of a plurality of material databases;

enumerating a plurality of possible synthetic reactions for the target inorganic material in a synthesis reaction enumerator module;

inputting the structural data and thermodynamic data for reactants for the possible synthetic reactions from any of the plurality of material databases to a synthesis reaction enumerator module;

constructing a synthesis reaction database for the target inorganic material from the plurality of possible synthetic reactions that yield the target inorganic material from the reactants;

entering each of the synthetic reactions from the synthesis reaction database into a competing phase finder module and a nucleation estimator module, the nucleation estimator module being configured for:

acquiring enthalpy and entropy data from at least one of the synthesis reaction enumerator module and any of the plurality of material databases and computing a reaction energy under a user-specified or a default thermodynamic condition and storing a viable subset of synthesis reactions where each of the synthetic reactions has a favorable value for the reaction energy;

computing similarity values for the reactants and the target inorganic material for each of the synthetic reactions of the viable subset of synthetic reactions from the structural data contained within the synthesis reaction database; and identifying epitaxially matching facets for the reactants and the target inorganic material for each of the synthetic reactions of the viable subset of synthetic reactions within the synthesis reaction database and store as a minimal matching area or a derived metric;

computing a nucleation barrier related metric for each synthetic reaction of the viable subset in the nucleation estimator module;

computing a number of possible thermodynamically competing phases for each synthetic reaction of the viable subset as a competition metric in a competition module; and outputting results of the nucleation estimator module as the nucleation barrier metric and results from the competing phase module as the competition metric to a recommendation visualizer where the viable subset of synthetic reactions is presented to the user in a mode displaying recommended synthetic reactions.

10. The computational method according to claim 9, wherein the structural data and thermodynamic data is tabulated and retrievable empirical data or first-principle computational data, where the computational data is retrieved from Materials Project, Open Quantum Materials Database, or AFLOW database, or a first-principle computational database is generated within a domain of the processor or on world wide web accessible computation systems.

11. The computational method according to claim 9, wherein enumerating comprises calculating stoichiometric and balanced reactions to the target inorganic material from a plurality of all possible synthetic reactions.

12. The computational method according to claim 9, wherein computing the reaction energy for each of the synthesis reactions stored in the synthesis reaction database comprises retrieval of thermochemical data of entries in each reaction from at least one of the plurality of material databases, and calculating the energy of the reaction from the acquired data and a user-specified or a default thermodynamic condition, and storing the viable subset of synthesis reactions.

13. The computational method according to claim 9, wherein computing similarity values comprises applying a similarity measure or using an inverse relationship with Euclidean or a non-Euclidean distance measure, measured in a high-dimensional representation space derived from one or more descriptors or by a crystal structure representation method for each of the reactants and the target inorganic material in the subset of viable reactions stored in the synthesis reaction database, wherein two similar materials have a short relative distance and/or have high similarity values.

14. The computational method according to claim 9, wherein identifying epitaxially matching facets for the reactants and the target inorganic material from these materials' crystal structures for each of the synthetic reactions of the viable subset of synthesis reactions in the synthesis reaction database results in an epitaxial matching quantity as a minimal matching area or as a derived score for each such viable reaction.

15. The computational method according to claim 9, wherein the nucleation barrier metric comprises a value reflecting bulk reaction energy in competition with one or more surface/interphase energies, and a penalty term for transport features.

16. The computational method according to claim 9, wherein computing the number of possible thermodynamically competing phases comprises identifying competing phases accessible from the reactants to the target inorganic material for each of the viable subset of synthesis reactions, and determining if a competing reaction energy to form the competing phase is thermodynamically favorable, and counting each competing phase having a competing reaction energy that is favorable.

17. The computational method according to claim 9, wherein the recommendation visualizer presents the synthetic reactions in the viable subset as a plot of their nucleation barrier metric vs. their competition metric wherein the synthetic reactions at or near an origin or on or near a pareto frontier comprise the synthetic reactions that are recommended.

18. The computational method according to claim 9, further comprising preparing a recommendation for an intermediate reactant, wherein the inorganic synthesis identifying program is used recursively for formation of the target inorganic material in a multistep process.

19. A non-transitory computer-readable medium for determining an optimal solid-state synthetic method for synthesis of an inorganic material and storing instructions that, when executed by one or more processors, cause the one or more processors to:

receive a target inorganic material from a user or from an output from a program in a processor;

query structural data and thermodynamic data for the target inorganic material from any of a plurality of material databases;

enumerate a plurality of possible synthetic reactions for the target inorganic material in a synthesis reaction enumerator module;

input the structural data and thermodynamic data for reactants for the possible synthetic reactions from any of the plurality of material databases to a synthesis reaction enumerator module;

construct a synthesis reaction database for the target inorganic material;

enter each of the possible synthetic reactions into a competing phase finder module and a nucleation estimator module, the nucleation estimator module being configured for:

acquiring enthalpy and entropy data, computing a reaction energy for each of the possible reactions and storing a viable subset of synthetic reactions from the synthesis reaction enumerator module;

computing similarity values for the reactants and the target inorganic material for each of the synthetic reaction of the viable subset of synthetic reactions from the structural data contained within the synthesis reaction database; and identifying epitaxially matching facets for the reactants and the target inorganic material for each synthetic reaction of the stored viable subset;

computing a nucleation barrier related metric for each synthetic reaction of the viable subset of synthetic reactions in the nucleation estimator module;

computing a number of possible thermodynamically competing phases for each synthetic reaction of the viable subset of synthetic reactions as a competition metric in a competition module; and output results of the nucleation estimator module as the nucleation barrier metric and results from the competing phase module as the competition metric to a recommendation visualizer where the viable subset is presented to the user in a mode displaying recommended synthetic reactions.

* * * * *